US011596662B2

(12) United States Patent
Leclere-Bienfait et al.

(10) Patent No.: US 11,596,662 B2
(45) Date of Patent: Mar. 7, 2023

(54) PASSION FLOWER SEED EXTRACT, AND COSMETIC, PHARMACEUTICAL OR DERMATOLOGICAL COMPOSITIONS CONTAINING SAME

(71) Applicant: LABORATOIRES EXPANSCIENCE, Paris la Défense (FR)

(72) Inventors: Sophie Leclere-Bienfait, Dreux (FR); Stéphanie Bredif, Croisilles (FR)

(73) Assignee: LABORATOIRES EXPANSCIENCE, Paris la Défense (FR)

( * ) Notice: Subject to any disclaimer, the term of this patent is extended or adjusted under 35 U.S.C. 154(b) by 202 days.

(21) Appl. No.: 17/239,042

(22) Filed: Apr. 23, 2021

(65) Prior Publication Data

US 2021/0236574 A1  Aug. 5, 2021

Related U.S. Application Data

(62) Division of application No. 16/064,312, filed as application No. PCT/EP2016/082216 on Dec. 21, 2016, now abandoned.

(30) Foreign Application Priority Data

Dec. 21, 2015 (FR) ...................................... 1562949

(51) Int. Cl.
| | | |
|---|---|---|
| A61K 36/185 | (2006.01) | |
| A61K 8/49 | (2006.01) | |
| A61Q 17/04 | (2006.01) | |
| A61Q 19/08 | (2006.01) | |
| A61Q 19/06 | (2006.01) | |
| A61Q 17/00 | (2006.01) | |
| A61K 8/9789 | (2017.01) | |
| A61P 17/16 | (2006.01) | |
| A61P 29/00 | (2006.01) | |
| A61K 8/368 | (2006.01) | |
| A61K 31/192 | (2006.01) | |
| A61K 31/353 | (2006.01) | |
| A61Q 19/00 | (2006.01) | |

(52) U.S. Cl.
CPC ............ *A61K 36/185* (2013.01); *A61K 8/368* (2013.01); *A61K 8/498* (2013.01); *A61K 8/9789* (2017.08); *A61K 31/192* (2013.01); *A61K 31/353* (2013.01); *A61P 17/16* (2018.01); *A61P 29/00* (2018.01); *A61Q 17/00* (2013.01); *A61Q 17/04* (2013.01); *A61Q 19/004* (2013.01); *A61Q 19/06* (2013.01); *A61Q 19/08* (2013.01); *A61K 2236/00* (2013.01); *A61K 2236/15* (2013.01); *A61K 2236/53* (2013.01); *A61K 2236/55* (2013.01)

(58) Field of Classification Search
CPC ........ A61Q 19/06; A61Q 17/04; A61Q 17/00; A61Q 19/004; A61K 31/192; A61K 36/185; A61K 8/368; A61K 8/9789; A61K 31/353; A61K 8/498; A61K 2236/00; A61K 2236/15; A61K 2236/53; A61K 2236/55; A61P 17/16; A61P 29/00
See application file for complete search history.

(56) References Cited

U.S. PATENT DOCUMENTS

| | | |
|---|---|---|
| 2014/0039049 A1 | 2/2014 | Sano et al. |
| 2016/0235794 A1 | 8/2016 | Leclere-Bienfait et al. |

FOREIGN PATENT DOCUMENTS

| | | | |
|---|---|---|---|
| CN | 103501640 A | 1/2014 | |
| CN | 104902962 A * | 9/2015 | ........... A61K 36/185 |
| EP | 2 415 743 A1 | 2/2012 | |
| EP | 2 700 322 A1 | 2/2014 | |
| FR | 3 010 906 A1 | 3/2015 | |
| JP | 2013-151457 A | 8/2013 | |
| JP | 2013-227256 A | 11/2013 | |
| KR | 10-2015-0064314 | 6/2015 | |
| WO | WO 2012/144064 A1 | 10/2012 | |

OTHER PUBLICATIONS

Bombardelli et al., "Passiflorine, A new Glycoside from Passiflora Edulis", Phytochemistry, vol. 14 (1975) pp. 2661-2665.
Chassagne et al., "A Cyanogenic Glycoside from Passiflora Edulis Fruits", Phytochemistry, vol. 49, No. 3 (1998) pp. 757-759.
De Meo et al., "Genotoxic Activity of Potassium Permanganate in Acidic Solutions", Mutation Research, vol. 260 (1991) pp. 295-306.
De Vasconcelos Vieira Lopes et al., "Physicochemical and Rheological Properties of Passion Fruit Oil and its Polyol", Eus. J. Lipid. Sci. Technol., vol. 112 (2010) pp. 1253-1262.
Dhawan et al., "Passiflora: a review update", Journal of Ethnopharmacology, vol. 94 (2004) pp. 1-23.
Lourith et al., "Antioxidant Activities and Phenolics of Passiflora edulis Seed Recovered from Juice Production Residue", J. Oleo Sci., vol. 62, No. 4 (2013) pp. 235-240.
Maruki-Uchida et al., "The Protective Effects of Piceatannol from Passion Fruit (*Passiflora edulis*) Seeds in UVB-Irradiated Keratinocytes", Biol. Pharm. Bull., vol. 36, No. 5 (2013) pp. 845-849.
Matsui et al., "Extract of Passion Fruit (*Passiflora edulis*) Seed Containing High Amounts of Piceatannol Inhibits Melanogenesis and Promotes Collagen Synthesis", J. Agric. Food Chem., vol. 58 (2010) pp. 11112-11118.

(Continued)

*Primary Examiner* — Aaron J Kosar
(74) *Attorney, Agent, or Firm* — Birch, Stewart, Kolasch & Birch, LLP

(57) ABSTRACT

The invention relates to a polyphenolic extract of passion flower seeds, in particular *Passiflora incarnata* or *Passiflora edulis* seeds, comprising at least 30 percent by weight polyphenols, expressed as gallic acid equivalent, relative to the weight of the dry extract. The invention also relates to a method for preparing an extract of said type, a composition containing same, and the cosmetic, dermatological or therapeutic use thereof.

22 Claims, 8 Drawing Sheets

(56) References Cited

OTHER PUBLICATIONS

Matsui et al., "Seeking a New Anti-Skin-Aging Material: Piceatannol and Its Derivatives from Passion Fruit (*Passiflora edulis*) Seed", American Chemical Society Symposium Series, Washington, D.C., (2013) pp. 189-202.

Morais et al., "Antioxidant activity, phenolics and UPLC-ESI(−)-MS of extracts from different tropical fruits parts and processed peels", Food Research International, 2015 (available online Sep. 1, 2015), vol. 77, pp. 392-399 ( 9 pages).

Patel, "Morphology and Pharmacology of Passiflora Edulis: A Review", Journal of Herbal Medicine and Toxicology, vol. 3, No. 1 (2009) pp. 1-6.

Piombo et al., "Characterization of the Seed Oils from Kiwi (*Actinidia chinensis*), Passion Fruit (*Passiflora edulis*) and Guava (*Psidium guajava*)" OCL, vol. 13, No. 2-3 (2006) pp. 195-199.

Rudnicki et al., "Antioxidant and antiglycation Properties of Passiflora alata and Passiflora edulis extracts", Food Chemistry, vol. 100 (2007) pp. 719-724.

Sano et al., "Identification of the Strong Vasorelaxing Substance Scirpusin B, a Dimer of Piceatannol, from Passion Fruit (*Passiflra edulis*) Seeds", Journal of Agricultural and Food Chemistry, vol. 59 (2011) pp. 6209-6213.

Seigler et al., "Cyanogenic Allosides and Glucosides from Passiflora Edulis and Carica Papaya", Phytochemistry, vol. 60 (2002) pp. 873-882.

Singh et al., "A Simple Technique for Quantitation of Low Levels of DNA Damage in Individual Cells", Experimental Cell Research, vol. 175 (1988) pp. 184-191.

Zeraik et al., "Quantification of Isoorientin and Total Flavonoids in Passiflora Edulis Fruit Pulp by HPLC-UV/DAD", Microchemical Journal, vol. 96 (2010) pp. 86-91.

\* cited by examiner

Negative control

PASSION FLOWER SEED EXTRACT, AND COSMETIC, PHARMACEUTICAL OR DERMATOLOGICAL COMPOSITIONS CONTAINING SAME

CROSS-CITE TO RELATED APPLICATIONS

This application is a Divisional of copending application Ser. No. 16/064,312, filed on Jun. 20, 2018, which is the National Phase under 35 U.S.C. § 371 of International Application No. PCT/EP2016/082216, filed on Dec. 21, 2016, which claims the benefit under 35 U.S.C. § 119(a) to Patent Application No. 1562949, filed in France on Dec. 21, 2015, all of which are hereby expressly incorporated by reference into the present application.

The invention relates to an extract of seeds of passion flower, *Passiflora incarnata* or *edulis*, preferentially *edulis*, particularly polyphenol-rich, and to a method for preparing such an extract. The present invention further relates to the cosmetic, dermatological or therapeutic use of such a composition or such an extract. Finally, the invention relates to a method for cosmetic care of the skin, the skin appendages or the mucous membranes, consisting in administering such a composition or such an extract.

Passion Flowers

There are roughly 500 species of passion flowers (genus *Passiflora*). These species are often distributed in hot, temperate and tropical regions, particularly in the Americas, but they are rather rare in Asia, Australia and tropical Africa.

Botany

The plants are in the form of shrubs or vines. The leaves are alternate, sometimes simple, lobed or palmate. The flowers can reach 9 cm in diameter and are bisexual or unisexual and regular. They are white and purple with thin petals trimmed with filiform appendices resembling Christ's crown of thorns. The 4-to 5-cm-long fruit is oval and often yellow to orange in colour.

The most widespread species are notably *Passiflora incarnata* (*P. incarnata*) and *Passiflora edulis* (*P. edulis*).

Phytochemical Aspects

*P. incarnata*: the major constituents are flavonoids, which are present in large amounts in the leaves. The leaves contain a high isovitexin content in particular. *P. incarnata* leaves also contain a small amount of simple indole alkaloids (harmane, harmine, etc.), sugars such as raffinose, sucrose, fructose and glucose, essential oils, and maltol, which is described as the molecule responsible for the sedative and anticonvulsive effects attributed to this plant.

*P. edulis*: a specific compound, passiflorine (cyclopropane triterpene glycoside), has been identified from a methanolic extract of dried leaves (E. Bombardelli et al., 1975).

*P. edulis* leaves contain isoorientin in particular, a flavonoid not found in the species *P. incarnata*. They also contain traces of essential oil and of alkaloids identical to the species *P. incarnata*.

The fruit's flesh contains flavonoids (schaftoside, isoschaftoside, isoorientin, orientin, isovitexin), luteolin derivatives (M. L. Zeraik, J. H. Yariwake—2010), and ascorbic acid (roughly 60 mg/100 g).

The flesh also contains glycosylated cyanogenic derivatives: prunasin, sambunigrin and amygdalin, and two recently-identified mandelonitrile β-rutinosides (D. Chassagne and J. Crouzet, 1998; D. S. Seigler, 2002).

Toxicology

Cyanogenic constituents are present chiefly in the aerial parts of various passion flower varieties.

Seed Characteristics

The seeds make up 6% to 12% of the *P. Edulis* fruit and contain:

polyphenols, including piceatannol (structure similar to resveratrol) and its dimer scirpusin B (S. Sano; K. Sugiyama; T. Ito, 2011), substances having vasorelaxant and antioxidant effects.

oil (18% yield after solvent extraction) containing phytosterols (0.2%, including campesterol, stigmasterol, sitosterol, avenasterol); 60% to 73% linoleic acid (omega 6), 14% to 20% oleic acid and 465 ppm tocopherol (G. Piobom, N. Barou et al., 2006; R. de V. V. Lopes et al.).

sugars and proteins.

PRIOR ART

Dietary Use

The fruit is believed to have been consumed since prehistoric times. In 16th century Peru the magnificent passion flowers were already regarded as a remedy, and numerous passion flower species are still used in many countries in common therapeutic practices.

Medical Use

Passion flowers (often the aerial parts and sometimes the fruit) are often used throughout the world as anxiolytic, sedative, diuretic or analgesic ("*Passiflora*: review update. K. Dhawan, S. Dhawan, A. Sharma, 2004"). Maltol and certain maltol derivatives are responsible for this sedative effect.

This activity is more constant and more significant for the species *P. incarnata*.

*P. incarnata* extracts are capable of reversing morphine dependence.

An antihypotensive effect of a methanolic extract of *P. edulis* fruit peel and a hypocholesterolaemia effect of a fibre-rich extract of defatted seeds have also been shown.

An antitumour effect of a fruit decoction via inhibition of matrix metalloproteinases (MMP2 and MMP9) involved in tumour invasion, metastases and angiogenesis, has also been shown (S. S. Patel, 2009).

Dermo-Cosmetic Uses

In Brazil, *P. foetida* leaves are used topically to treat inflammatory skin disorders, in particular by virtue of the presence of isoorientin. In Mauritius and Rodrigues, decoctions of *P. suberosa* leaves are also used in the bath to treat skin conditions.

DESCRIPTION OF THE INVENTION

The Applicant has discovered that extracts of seeds of passion flower, in particular *Passiflora incarnata* or *Passiflora edulis*, and advantageously *Passiflora edulis*, have cosmetic, pharmaceutical and dermatological properties that have hitherto never been disclosed. In particular, it is the first time that such passion flower seed extracts are used as such, for their specific properties.

The invention thus relates to a polyphenolic extract of seeds of passion flower, in particular of seeds of *Passiflora incarnata* or of *Passiflora edulis*, more particularly of *Passiflora edulis*, comprising at least 30 wt % polyphenols, expressed as gallic acid equivalents, relative to the weight of the dry extract. This content is equivalent to at least 3 mg of polyphenols per millilitre of liquid extract.

The polyphenol content is expressed as gallic acid equivalents, relative to the weight of the dry extract. These percentages are obtained by a Folin-Ciocalteu assay.

In a Folin-Ciocalteu assay, all phenolic compounds are oxidized by the Folin-Ciocalteu reagent (commercially available). The latter comprises a mixture of phosphotungstic acid ($H_3PW_{12}O_{40}$) and phosphomolybdic acid ($H_3PMo_{12}O_{40}$) which is reduced, during oxidation of the phenolic substances, to a mixture of blue oxides of tungsten ($W_8O_{23}$) and molybdenum ($Mo_8O_{23}$). The resultant blue colouring has a maximum absorption around 750-760 nm. It is proportional to the amount of oxidized phenolic compounds. The reference phenol used in this method is gallic acid (see, e.g., Singleton et al., *Colorimetry of total phenolics with phosphomolybdic-phosphotungstic acid reagents*). The results obtained by this assay are thus expressed as "wt % polyphenols, expressed as gallic acid equivalents, relative to the total weight of the dry extract".

The polyphenol content is thus an easily measurable parameter for persons skilled in the art.

The extract of the present invention advantageously comprises at least 35 wt % polyphenols, expressed as gallic acid equivalents, relative to the total weight of said dry extract, i.e., at least 3.5 mg of polyphenols per millilitre of liquid extract.

The extract of the present invention more advantageously comprises at least 40 wt % polyphenols, expressed as gallic acid equivalents, relative to the total weight of said dry extract, i.e., at least 4 mg of polyphenols per ml of liquid extract.

The majority of the polyphenols present in the extract of the invention are catechin derivatives.

The term "catechin derivatives", within the meaning of the present invention, refers to the flavonoids of the catechin family, also known as catechol. Catechin derivatives are more particularly compounds of the following general formula (I):

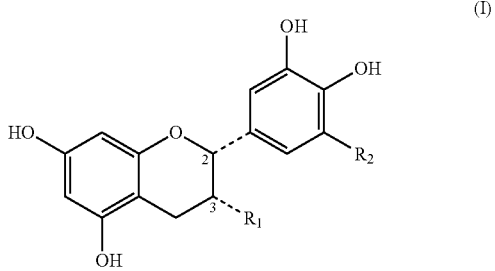

(I)

wherein:
- - - is a single bond of R or S configuration;
$R_1$ is OH or a galloyl group of the following formula (II):

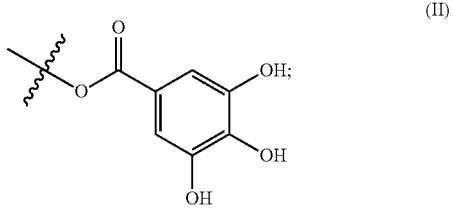 [SMILES: *OC(=O)c1cc(O)c(O)c(O)c1]

(II)

and
$R_2$ is H or OH.

Catechin derivatives are more particularly compounds of the general formula (I) selected from the group consisting of:

| Name | Configuration | $R_1$ | $R_2$ |
|---|---|---|---|
| (+)-catechin | 2R, 3S | OH | H |
| (−)-epicatechin | 2R, 3R | OH | H |
| (−)-catechin | 2S, 3R | OH | H |
| (+)-epicatechin | 2S, 3S | OH | H |
| (−)-epigallocatechin | 2R, 3R | OH | OH |
| (−)-epicatechin gallate | 2R, 3R | Galloyl group | H |
| (−)-epigallocatechin gallate | 2R, 3R | Galloyl group | OH |
| (+)-gallocatechin | 2R, 3S | OH | OH |
| (+)-gallocatechin gallate | 2R, 3S | Galloyl group | OH |

The extract of the invention advantageously comprises at least 20 wt %, in particular at least 24 wt %, catechin derivatives, expressed as gallic acid equivalents, relative to the weight of the dry extract. Thus, in the extract of the invention, at least 50 wt %, in particular at least 60 wt %, of the polyphenols are catechin derivatives, expressed as gallic acid equivalents, relative to the weight of polyphenols in the dry extract.

Advantageously, the extract of the invention further comprises at least 10 wt % organic acids, notably acetic acid, malic acid, citric acid or mixtures thereof, relative to the weight of the dry extract.

Particularly advantageously, the extract of the invention comprises at least 30 wt % polyphenols, expressed as gallic acid equivalents, relative to the weight of the dry extract, and at least 10 wt % organic acids, notably acetic acid, malic acid, citric acid or mixtures thereof, relative to the weight of the dry extract.

According to this aspect, the extract of the invention has the advantage of being rich in organic acids, which imparts to it high antioxidant, anti-chelating and/or hydrating activity.

The extract of the invention is advantageously obtained by solid/liquid extraction of passion flower seeds in a solvent selected from water, glycerols, glycols, and mixtures thereof.

The solvent is more particularly selected from the binary mixtures water/glycerol, water/glycol, and mixtures thereof, advantageously in a proportion of 30% to 90%, in particular of 40% to 90%, preferably of 50% to 90%, more preferentially of 60% to 80%, in particular of 70%, of glycerol and/or of glycol in water.

Preferably, the solvent used is selected from the binary mixtures water/glycerol or water/propanediol, in particular water/propanediol, more particularly water/1,3-propanediol.

In particular, the extract of the invention advantageously contains, by weight relative to the dry extract obtained:
- roughly 40% polyphenols;
- roughly 10% sugars;
- roughly 11% fruit acids; and
- roughly 5% proteins.

Particularly, the extract of the invention does not comprise isoorientin, orientin, vitexin or isovitexin.

The invention also relates to a method for preparing a polyphenolic extract of passion flower, in particular of seeds of *Passiflora incarnata* or of *Passiflora edulis*, advantageously of *Passiflora edulis*, comprising at least 30 wt % polyphenols, expressed as gallic acid equivalents, relative to the weight of the dry extract, said method comprising at least one step of solid/liquid extraction in a solvent selected from water, glycerols, glycols, and mixtures thereof.

Advantageously, said method for preparing a polyphenolic extract of passion flower seeds of the invention comprises the following successive steps:
- a) grinding the seeds;
- b) optionally defatting the seeds, preferably by pressing, ethanolic extraction or $CO_2$ extraction;
- c) solid/liquid extraction of the ground and optionally defatted seeds in a solvent selected from water, glycerols, glycols, and mixtures thereof;
- d) separating the solid phase and the liquid phase by decantation, and/or centrifugation and/or successive filtrations;
- e) optionally drying the extract obtained in step d).

Step a) of grinding the seeds can be performed by methods known to persons skilled in the art, notably using a knife mill, a hammer mill, etc.

In step c), the solid/liquid extraction phase is performed preferably at a temperature of 20° C. to 90° C., in particular of 30° C. to 80° C., more particularly of 45° C. to 75° C., typically of 70° C.

The extraction is performed for 30 minutes to 4 hours, in particular for 1 hour to 3 hours, advantageously for roughly 2 hours.

Advantageously, the extraction solvent used in step c) is selected from the binary mixtures water/glycerol, water/glycol, and mixtures thereof, advantageously in a proportion of 30% to 90%, in particular of 40% to 90%, preferably of 50% to 90%, more preferentially of 60% to 80%, in particular of 70%, of glycerol and/or of glycol in water. In particular, the extraction solvent is selected from the binary mixtures water/glycerol or water/propanediol, in particular water/propanediol, more particularly water/1,3-propanediol.

In an advantageous variant of the method, prior to step c), the passion flower seeds are defatted. Before being dispersed, the ground seeds can be defatted, notably in ethanol. Removal of the lipids allows better efficacy of the extraction and filtration steps. It is also and preferentially possible to use oil-cakes of these seeds, i.e., the residue resulting from preliminary extraction of the oil by solvent, using the supercritical $CO_2$ technique, for example, and preferentially by mechanical pressing.

Step d) of separating the solid phase and the liquid phase is performed by methods known to persons skilled in the art, notably by decantation, centrifugation and/or successive filtrations until perfect clarity and microbiological cleanliness are achieved.

Advantageously, the polyphenolic extract of the invention can be stabilized by the drying step e), by methods known to persons skilled in the art.

For example, the drying step can be performed in the presence of an additive of type maltodextrin or acacia fibre (Fibregum®, CNI), for example. The additive content typically varies from 0% to 80% additive relative to the percentage of dry matter obtained in the liquid form of the extract.

The extract is preferentially dried by lyophilization so as to obtain a final powder. The final powder advantageously comprises 30 to 70 wt % dry matter of the extract, the remainder to 100% being the lyophilization additive. More advantageously, the final powder comprises 50% dry matter derived from the extract and 50% lyophilization additive.

Alternatively, the starting raw material of the method of the invention can be an oil cake of defatted passion flower seeds, in particular defatted by pressing. Within this context and by way of non-limiting example, the polyphenolic extract of the invention can be obtained according to the following method:
- a') preparation of a solution of oil-cake of passion flower seeds defatted by pressing, at a concentration of 10% dry matter in water;
- b') solid/liquid extraction, with stirring, for 2 hours at a temperature of 70° C.;
- c') purification by successive filtrations; and
- d') sterile filtration.

The extract obtained by the method of the invention, as described in the preceding paragraphs, advantageously comprises at least 35 wt %, more advantageously at least 40 wt %, polyphenols, expressed as gallic acid equivalents, relative to the weight of the dry extract.

Advantageously, the extract obtained by the method of the invention also comprises at least 10 wt % organic acids, notably acetic acid, malic acid, citric acid or mixtures thereof, relative to the weight of the dry extract.

Advantageously, the extract obtained by the method of the invention comprises at least 20 wt %, in particular at least 24 wt %, catechin derivatives, expressed as gallic acid equivalents, relative to the weight of the dry extract. Thus, in the extract obtained by the method of the invention, at least 50 wt %, in particular at least 60 wt %, of the polyphenols are catechin derivatives, expressed as gallic acid equivalents, relative to the weight of polyphenols in the dry extract.

The present invention thus also relates to an extract of seeds of passion flower, in particular of seeds of *Passiflora incarnata* or of *Passiflora edulis*, advantageously of *Passiflora edulis*, obtainable by the above-mentioned method. Such an extract meets the specifications defined above concerning the extract of the invention.

In the description below, the expression "extract of the invention" refers to the extract as such, as defined above, or the extract obtainable by the method of the invention as described above.

The invention further relates to a composition comprising a polyphenol-rich extract of passion flower seeds of the invention, as active principle, and if necessary a suitable excipient. The extract of the invention is as defined in the paragraphs above concerning the extract as such and those concerning the extract obtainable by the method of the invention.

The composition of the invention advantageously comprises from 0.001 to 10 wt %, advantageously from 0.01 to 5 wt %, of said polyphenolic extract of passion flower seeds of the invention, the weight of the extract being expressed as dry extract, relative to the total weight of the composition.

The composition is advantageously cosmetic, pharmaceutical or dermatological. Said composition is preferably formulated to be administered via the external topical route.

The composition of the invention can further comprise one or more other active principles.

The composition of the invention can be formulated as various preparations suitable for topical administration.

In particular, the topical compositions can be notably creams, emulsions, milks, ointments, lotions, oils, aqueous or hydro-alcoholic or glycolic solutions, powders, patches, sprays, shampoos, varnishes or any other product for external application.

Depending on its nature (cosmetic, dermatological or pharmaceutical), the composition of the invention can further comprise at least one cosmetically, pharmaceutically or dermatologically acceptable excipient. Notably, the composition of the present invention can further comprise at least one cosmetically, pharmaceutically or dermatologically acceptable adjuvant known to persons skilled in the art, selected from surfactants, thickeners, preservatives, fragrances, dyes, chemical or mineral filters, hydrating agents, thermal spring water, etc. Persons skilled in the art can adapt the formulation of the composition of the invention based on their general knowledge.

The optimal modes of administration, dosing schedules and dosage forms of the compositions of the invention can be determined according to the criteria generally taken into account in the establishment of a pharmaceutical, dermatological or cosmetic treatment adapted to a patient or to an animal, such as, for example, the patient's or the animal's age or body weight, general state of health, tolerance to the treatment and skin type, and the side effects observed.

The invention also relates to an extract of the invention or a composition of the invention for use in preventing and/or treating conditions or diseases of the skin and/or of the mucous membranes and/or of the skin appendages, advantageously inflammatory reactions, oxidation reactions, disorders relating to radical attacks optionally linked to pollution, disorders of the barrier or of homeostasis, of ageing, notably of chronological and/or actinic ageing, of the skin and/or of the mucous membranes and/or of the skin appendages.

The invention also relates to an extract of the invention or a composition of the invention for use in preventing and/or treating vascular disorders and/or damaged adipose tissue.

The invention also relates to the use of a passion flower seed extract of the invention, or of a composition of the invention, in the manufacture of a cosmetic, pharmaceutical or dermatological composition for preventing and/or treating disorders or pathologies of the skin and/or of the mucous membranes and/or of the skin appendages, advantageously inflammatory reactions, oxidation reactions, disorders relating to radical attacks optionally linked to pollution, disorders of the barrier or of homeostasis, of ageing, notably of chronological and/or actinic ageing, of the skin and/or of the mucous membranes and/or of the skin appendages.

The invention also relates to the use of a passion flower seed extract of the invention, or of a composition of the invention, in the manufacture of a cosmetic, pharmaceutical or dermatological composition for preventing and/or treating vascular disorders and/or damaged adipose tissue.

The invention further relates to a method for preventing and/or treating disorders or pathologies of the skin and/or of the mucous membranes and/or of the skin appendages, advantageously inflammatory reactions, oxidation reactions, disorders relating to radical attacks optionally linked to pollution, disorders of the barrier or of homeostasis, of ageing, notably of chronological and/or actinic ageing, of the skin and/or of the mucous membranes and/or of the skin appendages, comprising the administration, in particular the topical administration, of an effective amount of a passion flower seed extract of the invention, or of a composition of the invention, to a subject in need thereof.

The invention further relates to a method for preventing and/or treating vascular disorders and/or damaged adipose tissue, comprising the administration, in particular the topical administration, of an effective amount of a passion flower seed extract of the invention, or of a composition of the invention, to a subject in need thereof.

In particular, the composition or the extract of the invention is intended for the prevention and/or treatment of inflammatory reactions, oxidation reactions, disorders related to radical attacks linked to environmental stress, such as pollution, UV radiation, cigarettes, etc., disorders of the barrier or of homeostasis, of ageing, notably of chronological and/or actinic ageing, of the skin, of the skin appendages (hair and nails) and/or of the mucous membranes (gums, periodontium, genital mucosa) whether immature, normal or mature/aged.

Notably, the composition or the extract of the invention is intended for the prevention and/or treatment of disorders related to inflammatory and/or radical reactions caused by exposure to UV radiation and/or to pollutants such as heavy metals, or related to intrinsic reactions, and thus generating accelerated ageing, disorders of the barrier, vascular disorders, blotches, etc.

Notably, the composition or the extract of the invention is intended for combatting skin ageing, notably chronological and/or actinic ageing.

In particular, the extract of the invention is intended to be used as antipollution cosmetic agent.

The expression "antipollution cosmetic agent" refers to an agent which protects the skin and the keratinous material so as to prevent, attenuate and/or eliminate the disorders or pathologies generated by toxic gases such as ozone and organic combustion residues. In particular, an antipollution cosmetic agent has an antioxidant and antiradical activity. The pollution concerned herein is in particular atmospheric pollution (such as ozone), outdoor pollutants (e.g., nitrogen dioxides, carbon monoxide, sulphur dioxide, ammonia, volatile organic compounds such as polycyclic aromatic hydrocarbons (e.g., benzo-α-pyrene)), indoor pollutants (e.g., volatile organic compounds, paint residues, biocontaminants, cigarette smoke, cooking smoke, construction materials, domestic cleaning or wood treatment products).

The above-mentioned skin disorders or pathologies are more particularly vascular disorders, atopic dermatitis, eczema, irritative dermatitis, sensitive skin, reactive skin, blotched skin, cutaneous erythema, aged or photoaged skin, photosensitive skin, sunburns and inflammations due to rays of any kind.

The invention also relates to a method for cosmetic care of the skin and/or of the skin appendages and/or of the mucous membranes, for the purpose of improving the condition and/or the appearance thereof, consisting in administering a composition or an extract of the present invention, advantageously via the external topical route.

The invention relates to a method for cosmetic care of the skin, for the purpose of preventing the ageing thereof, consisting in applying to the skin a composition or an extract of the present invention.

The invention also relates to a cosmetic treatment method for obtaining a protection of the organism against the effects of pollution, consisting in applying to the skin and to the skin appendages an extract or a composition of the invention, notably in a cosmetically effective amount.

The following examples illustrate the invention.

DESCRIPTION OF THE FIGURES

FIG. 11 shows the change in carbonylated protein content at T0 and at T28 in subjects having received the placebo or having received the active agent.

EXAMPLES

Example 1: Extract of the Invention

Figure 1:
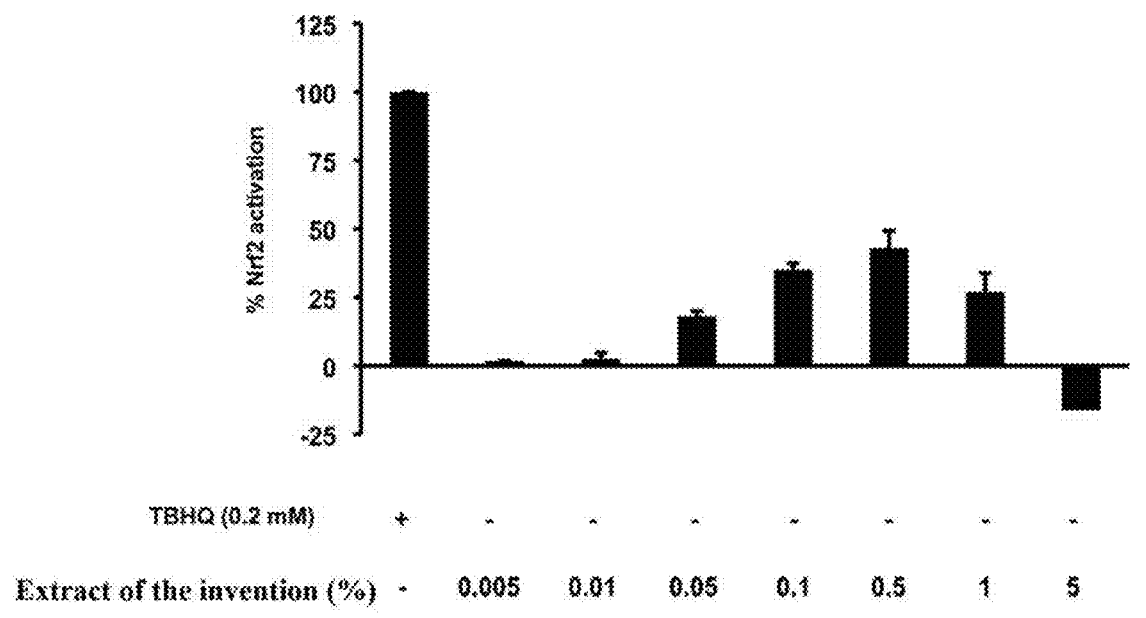
FIG. 1 shows the percentage of Nrf2 activation by an extract of the invention.
Figure 2:
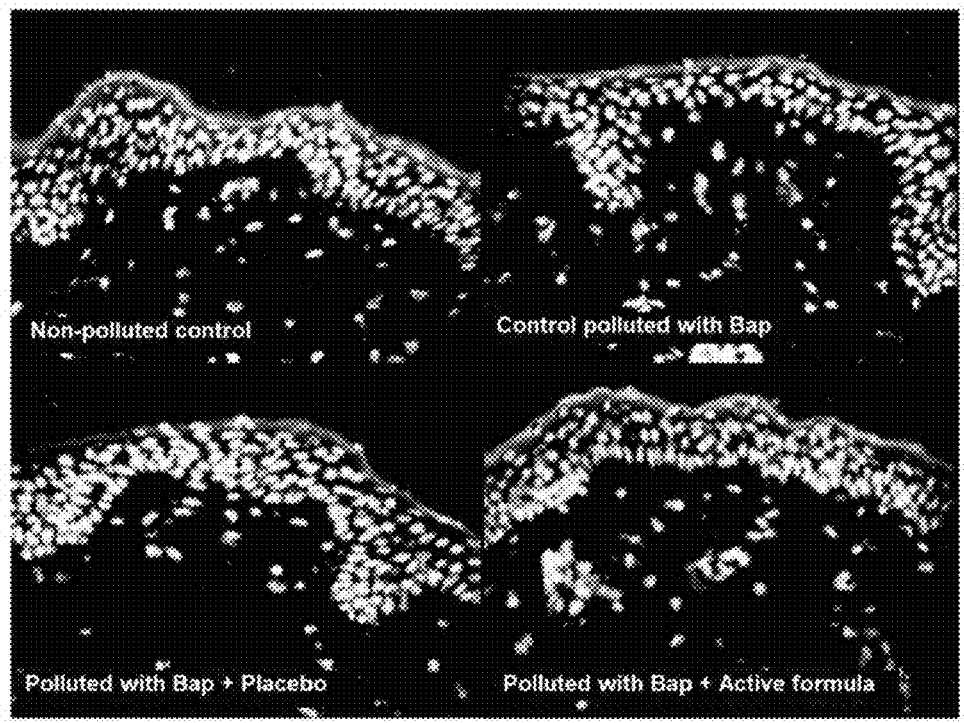
FIG. 2 shows claudin-4 immunostaining in skin explants treated with BaP (Protocol 1)
Figure 3:
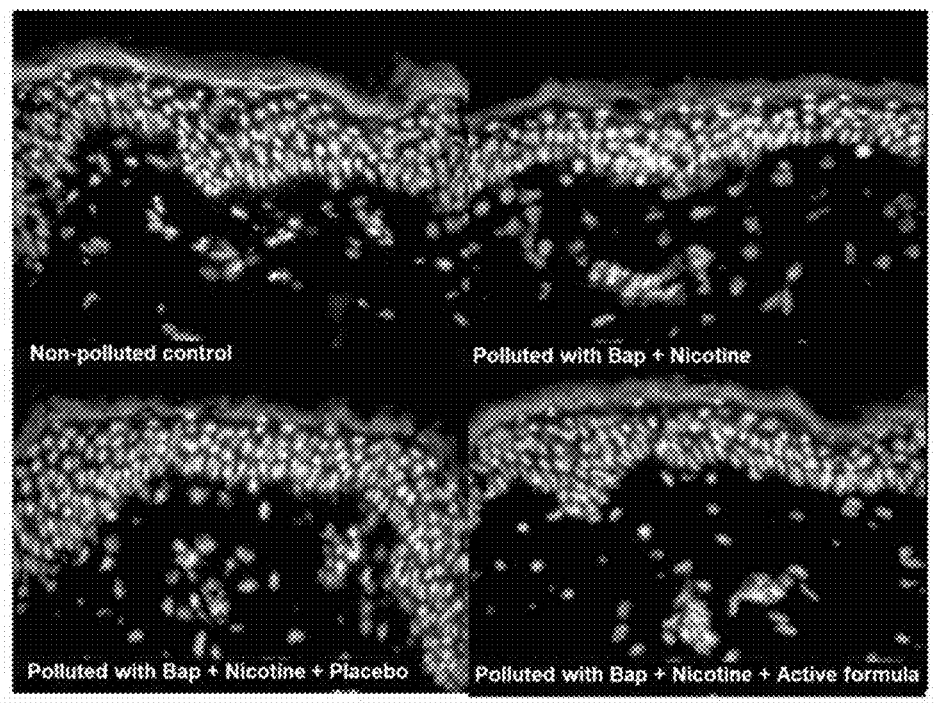
FIG. 3 shows filaggrin immunostaining in skin explants treated with BaP+nicotine (Protocol 2)
Figure 4:
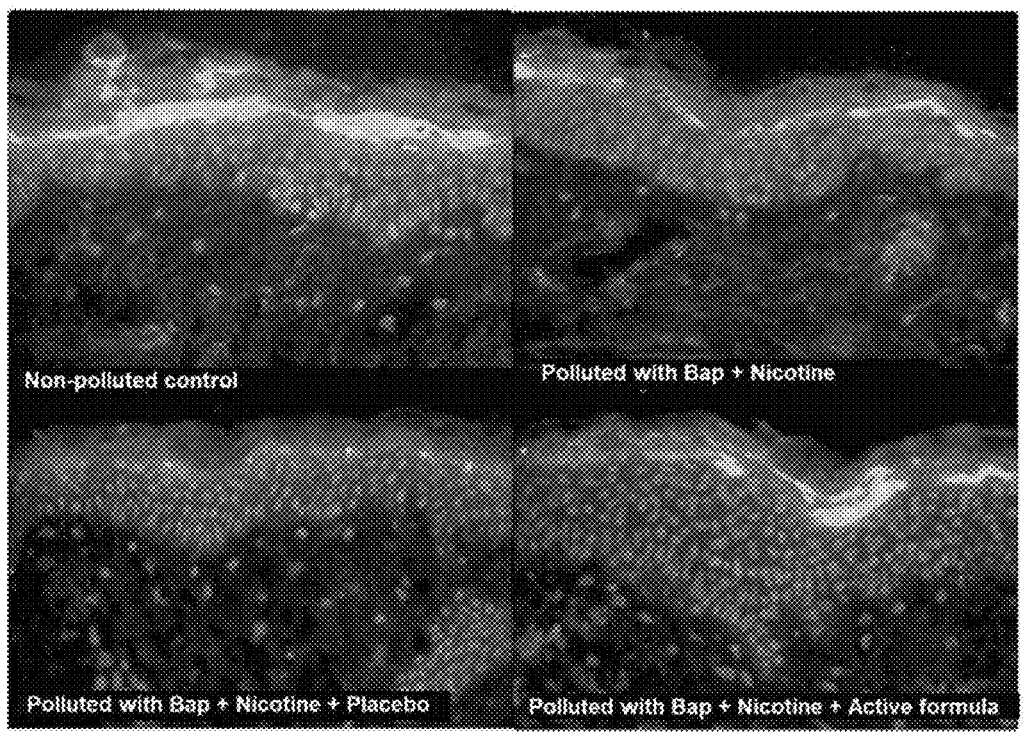
FIG. 4 shows loricrin immunostaining in skin explants treated with BaP+nicotine (Protocol 2)
Figure 5:
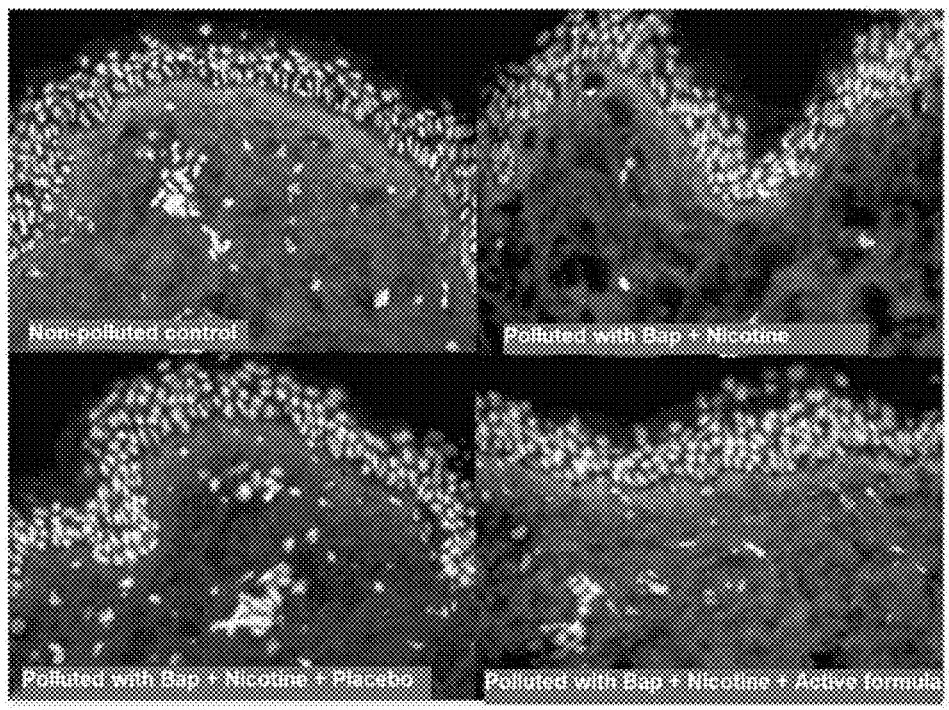
FIG. 5 shows collagen-I immunostaining in skin explants treated with BaP+nicotine (Protocol 2)
Figure 6:
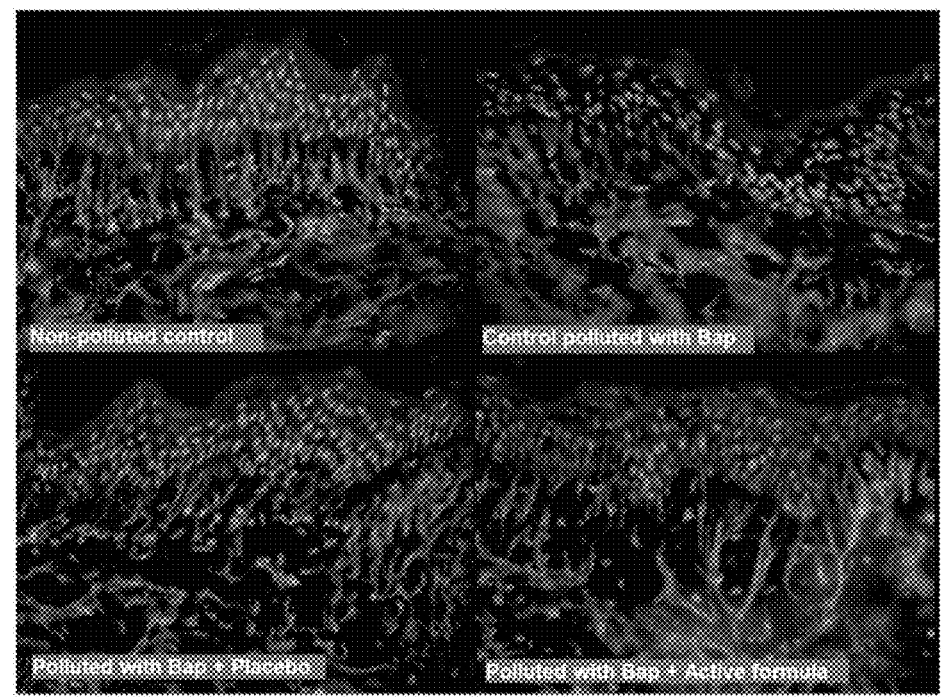
FIG. 6 shows elastin immunostaining in skin explants treated with BaP (Protocol 1)
Figure 7:
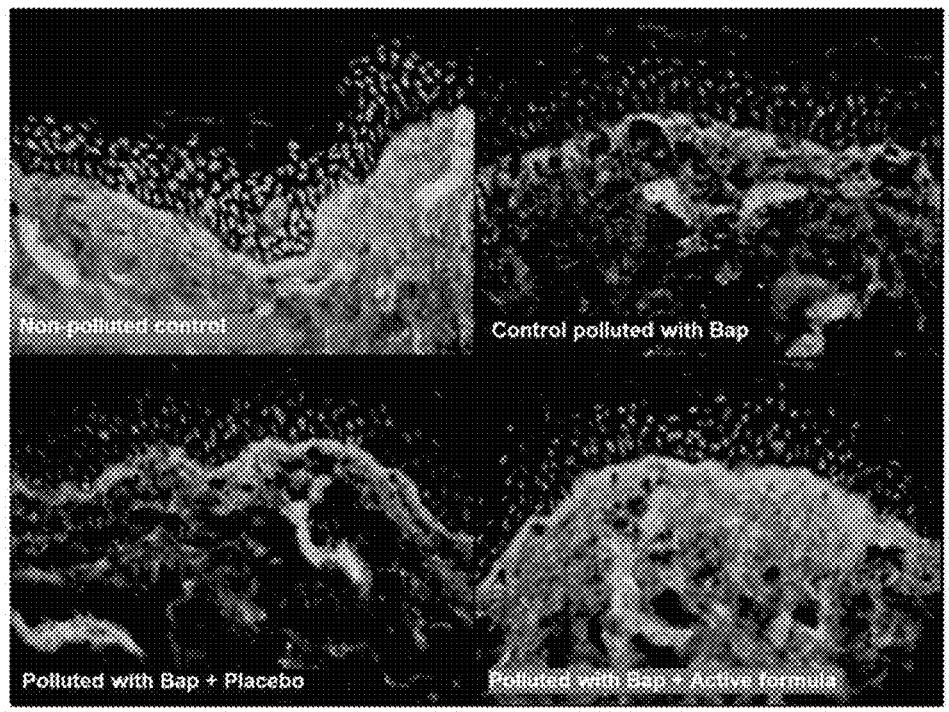
FIG. 7 shows fibronectin immunostaining in skin explants treated with BaP (Protocol 1)

A polyphenolic extract is obtained according to the following method:
  a) preparation of a solution of oil cake of *Passiflora edulis* seeds, defatted by pressing and ground (10% dry matter), in a 70:30 (w/w) 1,3-propanediol/water mixture;
  b) extraction with stirring for 2 hours at 70° C.;
  c) removal of the residual plant by coarse filtration; and
  d) purification of the extract obtained by filtrations including an additional sterile filtration.

The liquid polyphenolic extract thus obtained has the following characteristics (% of dry extract):
  Dry extract (drying chamber): 0.9% (m/m)
  Total polyphenol content (by spectrophotometry—in gallic acid equivalents): 43%
  Catechin derivative content (by HPLC—in gallic acid equivalents): 22.3%
  Malic acid content (by enzymatic kit): 5.4%
  Citric acid content (by enzymatic kit): 3.7%
  Protein content (by Kjeldahl×6.25): 4.5%

Example 2: Extract of the Invention

A polyphenolic extract is obtained according to the following method:
  a) preparation of a solution of 13.3% *Passiflora edulis* seeds, non-defatted and ground, in a 70:30 1,3-propanediol/water mixture
  b) extraction with stirring for 2 hours at 70° C.
  c) removal of the residual plant by coarse filtration
  d) purification of the extract obtained by filtrations, including an additional sterile filtration.

The liquid polyphenolic extract thus obtained has the following characteristics (% of dry extract):
  Dry extract (drying chamber): 1.07% (m/m)
  Total polyphenol content (by spectrophotometry—gallic acid equivalents): 40%
  Protein content (Kjeldahl×6.25): 5.7%

Example 3: Biological Activity of the Extract of the Invention

1. Biological Potential

The biological potential of an extract of the invention was investigated using a gene expression modulation test on normal human fibroblasts (NHF) and on reconstructed and melanized human epidermises.

Thus, the expression of 46 genes involved in various physiological pathways of the epidermis (barrier, pigmentation, inflammation, etc.) and of the dermis (scarring, elasticity, firmness, etc.) was studied by PCR-array.

Materials and Methods:

Normal human fibroblasts (NHF) and melanized reconstructed epidermises were incubated for 24 hours in the presence of an extract of the invention, as obtained in Example 1, at 0.002% and 0.05% (w/v) for the NHF or at 0.002% and 0.005% (w/v) for the reconstructed epidermises, and in the presence of 20 ng/ml TGF-β1 on the NHF or in the presence of 1 nM vitamin D3 on the reconstructed epidermises (controls for validating the tests).

At the end of the treatment, RNA was extracted and gene expression was analysed by qRT-PCR using the TaqMan array targeting the key functions of the dermis and of the epidermis.

Results and Conclusion:

The results are presented in Tables 2 and 3 below and show in particular that the extract of the invention, while varying the gene expression of certain markers, is of particular interest in the following activities:

the homeostasis and structure of the dermal extracellular matrix (↘ MMP3); and the dermo-epidermal junction (↗ LAMC2).

More particularly, the polyphenols of the extract of the invention enabled modulation of the expression of genes involved in antioxidant defences and the hormesis phenomenon (↗ HMOX1, FTL and G6PD).

This shows that the extract of the invention has antioxidant, antiradical and antiaging activity.

TABLE 2

| Screening on NHF | | | | |
|---|---|---|---|---|
| | Extract of the invention (0.002%) | | Extract of the invention (0.05%) | |
| | RQ* | p-value | RQ* | p-value |
| Haem oxygenase (HMOX1) | — | — | 4.0641 | 0.0025 |
| Ferritin, light polypeptide (FTL) | — | — | 2.3263 | 0.0221 |
| Glucose-6-phosphate dehydrogenase (G6PD) | | | 1.7197 | 0.0218 |
| Matrix metalloproteinase 1 (MMP1) | — | — | 0.6052 | 0.0282 |
| Matrix metalloproteinase 3 (MMP3) | 0.5513 | 0.0173 | — | — |

*Level of gene expression expressed as relative quantity (RQ) in relation to the untreated control = 1

TABLE 3

| Screening on reconstructed epidermises | | | | |
|---|---|---|---|---|
| | Extract of the invention (0.002%) | | Extract of the invention (0.05%) | |
| | RQ* | p-value | RQ* | p-value |
| Laminin subunit gamma-2 (LAMC2) | 2.2309 | 0.0387 | 4.1885 | 0.0165 |
| Proopiomelanocortin (POMC) | 2.3447 | 0.0398 | 1.7019 | 0.0183 |

TABLE 3-continued

Screening on reconstructed epidermises

| | Extract of the invention (0.002%) | | Extract of the invention (0.05%) | |
|---|---|---|---|---|
| | RQ* | p-value | RQ* | p-value |
| Melanocyte-stimulating hormone receptor (MC1R) | 0.7109 | 0.0175 | 0.6188 | 0.0127 |
| Cytosolic phospholipase A2 (PLA2G4A) | 0.6829 | 0.0391 | — | — |
| L-Dopachrome tautomerase (DCT) | — | — | 0.4637 | 0.0296 |

*Level of gene expression expressed as relative quantity (RQ) in relation to the untreated control = 1

2. Activity on Induction of Hormesis and Cellular Detoxification

A hormetic molecule (or hormetin) is a substance having a biphasic effect, namely a beneficial effect at a low dose and the opposite effect at a high dose (e.g., prooxidant or antioxidant). A hormetin is also described as being a molecule which reproduces the effects of mild stress on the organism but which in return enables the cell to protect itself against future attacks and thus to protect the organism against various age-related diseases (cancers) or physical phenomena (skin ageing, poor healing, etc.) or harmful environmental effects (UV radiation, pollution, etc.).

The following analyses made it possible to study the activity on induction of hormesis and cellular detoxification of an extract of the invention.

A—Activation of Translocation of Transcription Factor Nrf2:

The effect of the extract of the invention was evaluated with respect to activation of translocation of Nrf2, precursor of the cascade responsible for the hormetic response and for certain detoxification pathways of the organism.

Materials and Methods

ARE-luciferase-transfected HaCaT keratinocytes, containing the antioxidant response element (ARE) plasmid NQO1, which is a specific plasmid for activation of Nrf2 and luciferase (reporter gene), were treated for 6 hours at 37° C. with an extract of the invention, as obtained in Example 1, at concentrations ranging from 0.01% to 0.0005% (w/v) and with a positive reference, 20 µM tert-butylhydroquinone.

At the end of the treatment, the cell monolayers are lysed, luciferase activity is assayed using a "Luciferase Assay Kit" from PROMEGA, and the protein content of each lysate is assayed using the Bradford method (BioRad).

Results and Conclusion

The results obtained are presented in Table 4 and in FIG. 1. These results show that the extract of the invention induced an increase in Nrf2 activity in the nuclei, and thus a translocation of Nrf2 across the nuclear membrane, showing activation of this transcription factor.

This shows that the extract of the invention has antioxidant, antiradical and antiaging activity.

TABLE 4

Nrf2 activity in ARE-luciferase HaCaT (RLU = relative luciferase activity)

| | Nrf2 activity (mean normalized RLU/µg of proteins) | Activation (%) | |
|---|---|---|---|
| Control | 0 | 0 | |
| Tert-butylhydroquinone (20 µM) | 23216.4 | 100 | *** |
| Extract of the invention (0.0005%) | 4149.6 | 18 | * |
| Extract of the invention (0.001%) | 8178.2 | 35 | *** |
| Extract of the invention (0.005%) | 9998.6 | 43 | *** |
| Extract of the invention (0.01%) | 6324.6 | 27 | *** |

* $0.01 < p < 0.05$;
** $0.001 < p < 0.01$;
*** $p < 0.001$ and ns = not significant vs control cells - one-way ANOVA followed by Dunnett's test B—Gene Expression of the Principal Markers of Hormesis and of Cellular Detoxification.

The effect of an extract of the invention was studied on the gene expression of various markers involved in the hormesis pathways and in cellular detoxification.

Materials and Methods:

Normal human fibroblasts were treated for 6 hours, 24 hours and 48 hours at 37° C. with a 0.005% and a 0.002% (w/v) extract of the invention, as obtained in Example 1.

At the end of the treatment, the gene expression of markers of hormesis (HMOX1, FTL, G6PD and Nrf2) and of markers involved in cellular detoxification (SOD1 and catalase) was analysed by quantitative real-time RT-PCR and normalized to the housekeeping gene HPRT (SybrGreen technology).

The results were statistically analysed by one-way ANOVA followed by Dunnett's test (GraphPad PRISM version 5.02 software, GraphPad Software, San Diego, Calif., USA).

Results:

The results obtained are presented in Table 5. These results show that the extract of the invention significantly stimulated the gene expression of HMOX1 at 6 hours and 24 hours, of FTL at three times, of G6PD at 6 hours and 24 hours, of SOD1 at 24 hours, of Nrf2 at 24 hours and 48 hours, and of catalase at 24 hours.

This shows that the extract of the invention has antioxidant, antiradical and antiaging activity.

TABLE 5

Gene expression of hormesis markers in normal human fibroblasts (relative quantity)

| | HMOX1 | FTL | G6PD | SOD1 | Nrf2 | Catalase |
|---|---|---|---|---|---|---|
| 6 hours | | | | | | |
| Control cells | 1.00 | 1.00 | 1.00 | 1.00 | 1.00 | 1.00 |
| Extract of the invention (0.002%) | 3.38 (+238% ***) | 0.94 (−6% ns) | 1.31 (+31% *) | 1.03 (+3% ns) | 1.00 (+0% ns) | 0.97 (−3% ns) |

TABLE 5-continued

Gene expression of hormesis markers in normal human fibroblasts (relative quantity)

|  | HMOX1 | FTL | G6PD | SOD1 | Nrf2 | Catalase |
|---|---|---|---|---|---|---|
| Extract of the invention (0.005%) 24 hours | 23.06 (+2206% ***) | 1.37 (+37% ***) | 1.31 (+31% *) | 1.05 (+5% ns) | 1.04 (+4% ns) | 1.02 (+2% ns) |
| Control cells | 1.00 | 1.00 | 1.00 | 1.00 | 1.00 | 1.00 |
| Extract of the invention (0.002%) | 1.66 (+66% ***) | 1.62 (+62% **) | 1.41 (+41% ns) | 1.13 (+13% ns) | 1.25 (+25% *) | 1.23 (+23% ns) |
| Extract of the invention (0.005%) 48 hours | 2.68 (+168% ***) | 2.40 (+140% ***) | 1.70 (+70% **) | 1.33 (+33% *) | 1.30 (+30% *) | 1.31 (+31% *) |
| Control cells | 1.00 | 1.00 | 1.00 | 1.00 | 1.00 | 1.00 |
| Extract of the invention (0.002%) | 0.98 (−2% ns) | 1.10 (+10% ns) | 0.88 (−12% ns) | 1.39 (+39% ns) | 1.34 (+34%*) | 1.06 (+6% ns) |
| Extract of the invention (0.005%) | 1.00 (0% ns) | 1.66 (+66% ***) | 0.86 (−14% ns) | 0.97 (−3% ns) | 1.26 (+26% ns) | 1.04 (+4% ns) |

\* $0.01 < p < 0.05$;
\*\* $0.001 < p < 0.01$;
\*\*\* $p < 0.001$ and ns = not significant vs control cells - one-way ANOVA followed by Dunnett's test C—Production of Haem Oxygenase:

An extract of the invention was analysed on the protein expression of haem oxygenase.

Materials and Methods:

Normal human fibroblasts were treated for 24 hours with a 0.002% and a 0.005% (w/v) extract of the invention, as obtained in Example 1, and with 5 and 10 µM curcumin (reference hormetin).

At the end of the treatment, intracellular haem oxygenase 1 (or HMOX1 or H01) was quantified using an ELISA technique. Staining, proportional to the quantity of the marker of interest, was measured by reading the optical density (OD) at 450 nm, and the value obtained was related to the quantity of cells obtained by a protein assay using the BC Assay (Interchim).

The results were statistically analysed by one-way ANOVA followed by Dunnett's test (GraphPad PRISM version 5.02 software, GraphPad Software, San Diego, Calif., USA).

Results:

The results obtained are presented in Table 6. These results show that the extract of the invention induces the production of haem oxygenase 1 with the same intensity as does curcumin. This result confirms the action of the extract of the invention which we observed during the study of gene expression of this same marker.

This shows that the extract of the invention has antioxidant, antiradical and antiaging activity.

TABLE 6

HMOX1 production by fibroblasts

|  | HMOX1 (ng/ml on quantity of cells) | Inhibition |
|---|---|---|
| Control cells | 0.033 ± 0.003 | |
| Curcumin (5 µM) | 0.060 ± 0.002 | 82% *** |

TABLE 6-continued

HMOX1 production by fibroblasts

|  | HMOX1 (ng/ml on quantity of cells) | Inhibition |
|---|---|---|
| Curcumin (10 µM) | 0.105 ± 0.006 | 218% *** |
| Extract of the invention (0.002%) | 0.056 ± 0.002 | 69% *** |
| Extract of the invention (0.005%) | 0.098 ± 0.004 | 197% *** |

\*\*\* $p < 0.001$ vs control cells - one-way ANOVA followed by Dunnett's test D- Production of haem oxygenase under Nrf2 siRNA conditions:

In order to verify whether the haem oxygenase activation pathway by an extract of the invention indeed passes through activation of Nrf2, the potential to induce production of haem oxygenase was verified in a system where Nrf2 expression is blocked (small interference RNA, or siRNA).

Materials and Methods:

Normal human fibroblasts were pretreated for 24 hours with Nrf2 siRNA and scrambled siRNA (control siRNA without action) and then, on each preceding condition, for 24 hours with a 0.005% (w/v) extract of the invention, as obtained in Example 1.

At the end of the treatment, intracellular haem oxygenase 1 (or HMOX1) was quantified using an ELISA technique. Staining, proportional to the quantity of the marker of interest, was measured by reading the optical density (OD) at 450 nm.

The results were statistically analysed by one-way ANOVA followed by Tukey's test (GraphPad PRISM version 5.02 software, GraphPad Software, San Diego, Calif., USA).

Results:

The results obtained are presented in Table 7. These results show that the stimulation of HMOX1 production induced by an extract of the invention is substantially decreased (−62%, p<0.001) when the Nrf2 pathway is partially blocked (Nrf2 siRNA).

The activity of an extract of the invention on the production of haem oxygenase thus indeed passes through the Nrf2 pathway.

This shows that the extract of the invention has antioxidant, antiradical and antiaging activity.

TABLE 7

HMOX1 production by fibroblasts - Comparative: scrambled siRNA vs Nrf2 siRNA

|  | HMOX1 (ng/ml) | Inhibition related to Nrf2 siRNA | |
|---|---|---|---|
| Control cells - scrambled | 3.371 ± 0.702 | — | — |
| Control cells - Nrf2 siRNA | 2.199 ± 0.089 | −35% | * |
| Extract of the invention (0.005%) - scrambled | 18.821 ± 0.316 | — | — |
| Extract of the invention (0.005%) - Nrf2 siRNA | 7.105 ± 0.131 | −62% | *** |

*** $p < 0.001$ vs control cells - one-way ANOVA followed by Tukey's test

E—Effect on Production of Reactive Oxygen Species (ROS):

The antioxidant potential of an extract of the invention with respect to $H_2O_2$ induction of reactive oxygen species was studied.

Materials and Methods:

Normal human keratinocytes were incubated for 24 hours in the presence of a 0.002%, a 0.005% and a 0.01% (w/v) extract of the invention, as obtained in Example 1, or of 500 μM vitamin C and 10 μM quercetin (reference antioxidants) before incorporation of the H2DCF-DA probe (incubation for 60 minutes).

The keratinocytes were then stimulated with 100 μM hydrogen peroxide ($H_2O_2$) for 20 minutes and the production of reactive oxygen species (ROS) was evaluated by measurement of fluorescence.

The results were statistically analysed by one-way ANOVA followed by Tukey's test (GraphPad PRISM version 5.02 software, GraphPad Software, San Diego, Calif., USA).

Results:

The results obtained are presented in Table 8. These results show that the extract of the invention significantly inhibited the production of ROS by keratinocytes in response to hydrogen peroxide ($H_2O_2$)-induced oxidant stress. The level of this antioxidant activity is equivalent to that of the two control antioxidants (vitamin C and quercetin).

This shows that the extract of the invention has antioxidant, antiradical and antiaging activity.

TABLE 8

ROS production in $H_2O_2$-treated keratinocytes

|  | ROS (fluorescence units) | Significance | |
|---|---|---|---|
| Control cells | 30752.921 ± 4555.136 | — | — |
| Stimulated cells ($H_2O_2$) | 44179.976 ± 7445.110 | +44% | *** |
| Reference (vitamin C) | 21719.018 ± 3174.253 | −51% | *** |
| Reference (quercetin) | 14367.847 ± 1790.753 | −67% | *** |
| Extract of the invention (0.002%) | 18769.676 ± 2780.206 | −58% | *** |
| Extract of the invention (0.005%) | 14404.891 ± 2974.938 | −67% | *** |
| Extract of the invention (0.01%) | 16531.685 ± 1902.378 | −63% | *** |

*** $p < 0.001$ - one-way ANOVA followed by Tukey's test

3. Protection Against the Harmful Effects of Pollution

The preceding results showed that an extract of the invention stimulates the production of haem oxygenase 1 via activation of translocation of transcription factor Nrf2. Consequently, the extract of the invention enabled antioxidant cellular protection via reduction of ROS formation induced by $H_2O_2$ stress.

The extract of the invention making it possible to stimulate skin defences, we evaluated their protective effect with respect to various environmental stresses, in this case pollution.

A—Effect on Oxidant Stress:

Materials and Methods:

Normal human keratinocytes were treated for 24 hours with a 0.002% (w/v) extract of the invention, as obtained in Example 1, 500 μM vitamin C and 10 μM quercetin (reference antioxidants), with 10 μM curcumin (reference hormetin) or with 10 μM resveratrol before incorporation of the H2DCF-DA probe (incubation for 45 minutes).

The keratinocytes were then stimulated with 9 μg/ml benzo-α-pyrene (BaP) for 20 minutes. ROS production was evaluated by measurement of fluorescence.

The significance of the results was verified by Student's t-test.

Results and Conclusion

The results obtained are presented in Table 9. These results show that the 0.002% extract of the invention inhibited ROS production by keratinocytes in response to oxidant stress induced by 6 and 9 μg/ml BaP.

Therefore, the extract of the invention exerts a protective effect with respect to pollution-induced oxidant stress. The extract of the invention thus has antioxidant, antiradical, antipollution and antiaging activity.

TABLE 9

ROS production in keratinocytes treated with 9 μg/ml BaP

|  | ROS (fluorescence units) | | Significance |
|---|---|---|---|
| Control cells | 4730 ± 324 | — | — |
| Stimulated cells (9 μg/ml BaP) | 16777 ± 1755 | +255% | *** |
| Reference (vitamin C) | 14089 ± 1719 | −16% | NS |
| Reference (quercetin) | 17140 ± 1930 | −32% | NS |
| 10 μM curcumin | 14065 ± 1231 | −16% | NS |
| 10 μM resveratrol | 20357 ± 503 | −21% | * |
| Extract of the invention (0.002%) | 11052 ± 1828 | 34% | ** |

* $p < 0.05$;
** $p < 0.01$;
*** $p < 0.001$ and ns = not significant - Student's t-test B—Protection of Skin Structures:

The ability of an extract of the invention to protect the integrity of the skin (dermis and epidermis) from the harmful effects of pollution was studied on human skin explants.

Materials and Methods:

Human skin explants from a 45-year-old woman were pretreated for 24 hours with a topical application of a cosmetic formula containing or not containing (placebo) 3% extract of the invention, as obtained in Example 1.

Said explants were then treated again with the cosmetic formulas in the presence of benzo-α-pyrene (BaP, 20 μM) for Protocol 1 or of Bap+nicotine (20 μM) for Protocol 2. Immunostainings of various skin structure markers were performed.

Results and Conclusion

The results obtained are presented in FIGS. 2 to 7.

The stress mimicking pollution induced by BaP±nicotine led to altered expression of the structural markers studied.

Under these conditions, the extract of the invention protected the following epidermal markers:

Claudin 4 (marker of the tight junctions/barrier function),

Filaggrin (marker of the barrier function and precursor of natural hydration factors), and Loricrin (marker involved in cell differentiation/barrier function);

And the dermal markers:

Collagen I (marker involved in skin firmness),

Elastin (marker involved in skin elasticity), and

Fibronectin (marker involved in dermal structure).

These results show a real protective effect of the structural integrity of the epidermis and of its barrier function as well as the maintenance of a normal structure of the dermis and therefore an overall skin protective effect against environmental pollution.

The extract of the invention thus has antioxidant, antiradical, antipollution and antiaging activity.

C—Evaluation of Detoxifying Activity with Respect to Ozone Stress

The protective and detoxifying potentials of an extract of the invention with respect to ozone stress were evaluated on reconstructed epidermises.

Materials and Methods:

Reconstructed human epidermises (RHE) were pretreated for 24 hours with a topical application of a cosmetic formula containing or not containing (placebo) 3% extract of the invention, as obtained in Example 1.

The epidermises were then subjected to stress with 0.5 to 1 ppm ozone.

The enzymatic activities of the detoxifying enzymes catalase, glutathione peroxidase (GPX) and superoxide dismutase (SOD) were quantified by a calorimetric (SOD and GPX) or fluorescence (catalase) ELISA method.

Lipid peroxidation was evaluated by the malondialdehyde (MDA) assay, performed by GC. DNA oxidation was evaluated by the 8-hydroxydeoxyguanosine (8-OHdG) assay, performed by colorimetry.

The results were statistically analysed by one-way ANOVA followed by Tukey's test (GraphPad PRISM version 5.02 software, GraphPad Software, San Diego, Calif., USA).

Results and Conclusion

Ozone stress induced overactivation of catalase, SOD and GPX enzymes; this increase attests to the ozone-induced oxidant stress.

Under these conditions, the extract of the invention significantly inhibited this overactivation.

In the absence of ozone stress (basal condition), the extract of the invention induces no inhibition of the activity of the detoxifying enzymes. This confirms that it is indeed a protective effect with respect to the induced stress and not an inhibition of the detoxification systems of the cell.

(Tables 10, 11 and 12).

Ozone stress induced oxidative damage expressed as an increase in 8-OHdG and in MDA. The extract of the invention significantly protects cell components from the oxidative damage induced by ozone stress by significantly inhibiting the production of 8-OHdG and of MDA. (Tables 13 and 14).

TABLE 10

Catalase activity in RHE optionally treated with ozone

| | Mean | % change | Tukey |
|---|---|---|---|
| Catalase assay under ozone stress conditions | | | |
| Control epidermises | 156.1 | 0 | |
| Ozone | 340.1 | 118 | $$$ |
| Placebo | 306.4 | −10 | ns |
| Extract of the invention (3%) | 244.2 | −28 | *** |
| Catalase assay under basal conditions | | | |
| Control | 181.8 | 0 | |
| Placebo | 250.3 | 38 | $$$ |
| Extract of the invention (3%) | 231.4 | 27 | $$ |

$$ $0.001 < p < 0.01$;
$$$ $p < 0.001$ vs control
** $0.001 < p < 0.01$;
*** $p < 0.001$ vs ozone

TABLE 11

GPX activity in RHE optionally treated with ozone

| | Mean | % change | Tukey |
|---|---|---|---|
| GPX assay under ozone stress conditions | | | |
| Control | 13.0 | 0 | |
| Ozone | 34.9 | 168 | $$$ |
| Placebo | 31.1 | −11 | * |
| Extract of the invention (3%) | 23.3 | −33 | *** |
| GPX assay under basal conditions | | | |
| Control | 13.0 | 0 | |
| Placebo | 12.3 | −6 | ns |
| Extract of the invention (3%) | 13.2 | 2 | ns |

$$$ $p < 0.001$ vs control - * $0.01 < p < 0.05$;
*** $p < 0.001$ vs ozone

TABLE 12

SOD activity in RHE optionally treated with ozone

| | Mean | % change | Tukey |
|---|---|---|---|
| SOD assay under ozone stress conditions | | | |
| Control | 5.7 | 0 | |
| Ozone | 13.0 | 130 | $$$ |
| Placebo | 9.5 | −27 | *** |
| Extract of the invention (3%) | 7.2 | −45 | *** |
| SOD assay under basal conditions | | | |
| Control - | 4.7 | 0 | |
| Placebo formula | 5.4 | 15 | $$ |
| Extract of the invention (3%) | 4.9 | 4 | ns |

$ $0.01 < p < 0.05$;
$$ $0.001 < p < 0.01$
$$$ $p < 0.001$ vs control
** $0.001 < p < 0.01$;
*** $p < 0.001$ vs ozone

TABLE 13

8-Oxo-dG assay in ozone-treated RHE

| | Mean | % change | Tukey |
|---|---|---|---|
| Control | 2.9 | 0 | |
| Ozone | 7.4 | 155 | $$$ |
| Placebo | 5.4 | −27 | ** |
| Extract of the invention (3%) | 3.7 | −51 | *** |

$$$ p < 0.001 vs control
* 0.01 < p < 0.05;
** 0.001 < p < 0.01;
*** p < 0.001 vs ozone

TABLE 14

MDA assay in ozone-treated RHE

| | Mean | % change | Tukey |
|---|---|---|---|
| Control | 96.6 | 0 | |
| Ozone | 251.4 | 160 | $$$ |
| Placebo | 204.0 | −19 | ** |
| Extract of the invention (3%) | 176.6 | −30 | *** |

$$$ p < 0.001 vs control
** 0.001 < p < 0.01;
*** p < 0.001 vs ozone

4. Protection Against Sun-Related Deleterious Effects

Ultraviolet (UV) and infrared (IR) rays penetrate the skin to varying depths and are responsible for, amongst other things, a decrease in skin firmness and an increase in the quantity of free radicals released, thus leading to premature skin ageing. Such rays are also responsible for the formation of melanomas and for skin immunosuppression.

The protective effect of an extract of the invention with respect to UV- or IR-induced stress was studied.

A—Protection Against UV-Induced DNA Damage (Comet Assay):

Maintenance of the nuclear integrity of the cell, with respect to UV radiation, was tested using the comet assay.

Materials and Methods:

Normal human keratinocytes were treated for 2 hours with a 0.001% (w/v) extract of the invention, as obtained in Example 1.

A comet assay is performed according to the method described by "Singh et al." in 1988 and by "Meo et al." in 1991, and which consists in irradiating cells with light at 4.5 J/cm$^2$ (0.28 J/cm$^2$ UVA; 0.08 J/cm$^2$ UVB and 4.14 J/cm$^2$ visible light) corresponding to 1 to 3 minutes of sun exposure in mid-summer. This is followed by DNA migration using agarose gel electrophoresis.

A relative value $\chi^2$ OTM is calculated using the Systat software, this value being directly proportional to the size of the comet and thus to the degree of protection of the active agent with respect to UV radiation.

The significance of the results was verified by analysis of variance using the SigmaPlot software (version 11.0, Systat Software, Chicago, Ill., USA).

Results and Conclusion

Figure 8A:
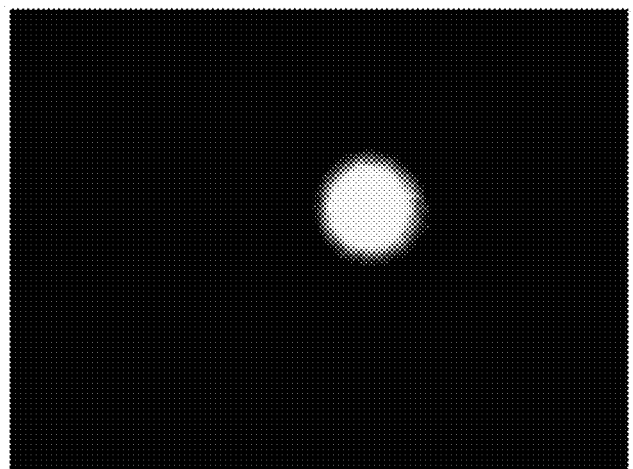
FIG. 8A corresponds to a negative control sample, FIG. 8B to a UV control sample and FIG. 8C to a 0.001% extract of the invention.
Figure 8B:
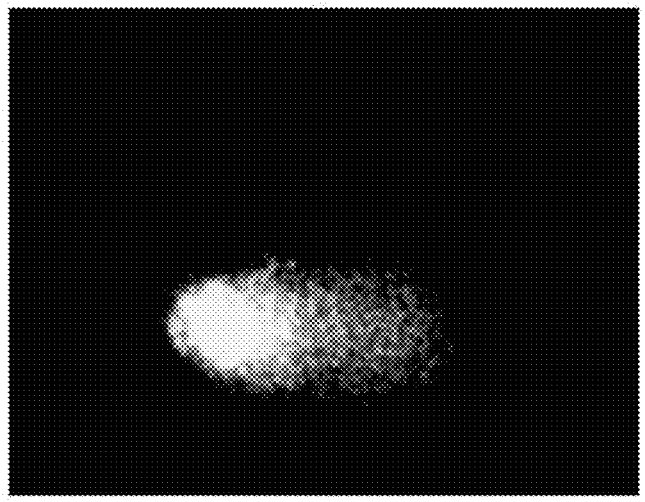
FIG. 8 shows the visual appearance of the comet assay after electrophoresis of treated normal human keratinocytes.
Figure 8C:
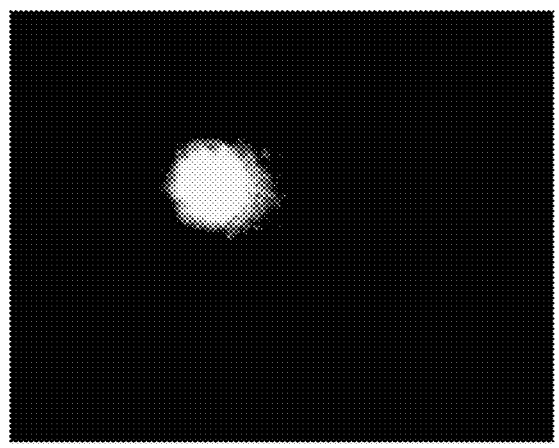

The results are presented in Table 15 and in FIG. 8.

These results show that the 0.001% extract of the invention protected keratinocytes with respect to UV-irradiation-induced DNA damage (54% protection, p<0.001).

The extract of the invention thus has antioxidant, antiradical, antipollution and antiaging activity.

TABLE 15

Percent protection of cells with respect to UV radiation

| | $\chi^2$ OTM | % protection | |
|---|---|---|---|
| Control without UV | 2.09 ± 0.1 | 100 | |
| Control irradiated at 4.5 J/cm$^2$ | 11.59 ± 0.41 | 0 | *** |
| Extract of the invention (0.001%) | 6.43 ± 0.28 | 54.4 | *** |

*** p < 0.001 vs non-irradiated cells and vs cells irradiated at 4.5 J/cm$^2$.
Statistics from SigmaPlot B—Inhibition of IR-Induced Production of MMP1

Infrared (IR) rays, which represents more half of the solar spectrum, can induce degradation of the dermal matrix, contributing to skin ageing, by stimulating the production of proteases such as MMP1.

The ability of an extract of the invention to protect dermal cells from the harmful effects of IR rays was studied by evaluating MMP1 production.

Materials and Methods:

Normal human fibroblasts (NHF) were incubated in the presence of a 0.001% extract of the invention, as obtained in Example 1, or of 10$^{-7}$ M dexamethasone (reference anti-inflammatory) for 48 hours following 1 hour of infrared irradiation (0.57 kJ/cm$^2$).

After incubation, the supernatants are collected in order to assay released MMP1 (ELISA Kit, R&D Systems).

The significance of the results was verified by Student's t-test.

Results and Conclusion

The results are presented in Table 16. These results show that the 0.001% extract of the invention significantly inhibited infrared-induced production of MMP1 in normal human fibroblasts.

The extract of the invention thus has antioxidant, antiradical, antipollution and antiaging activity.

TABLE 16

IR-induced production of MMP1 in normal human fibroblasts

| | MMP1 (ng/ml) | % protection | |
|---|---|---|---|
| Control without IR | 11 | 100 | *** |
| Control irradiated at 0.57 kJ/cm$^2$ | 88.6 | 0 | |
| Dexamethasone (10$^{-7}$M) | 9.3 | 102 | *** |
| Extract of the invention (0.001%) | 77.4 | 14 | * |

* p <0.05;
*** p < 0.001 vs irradiated cells

C—Protection Against UV-Induced Oxidant Stress:

The antioxidant potential of an extract of the invention with respect to UV-irradiation-induced reactive oxygen species (ROS) was studied.

Materials and Methods:

Normal human keratinocytes were incubated for 24 hours in the presence of a 0.001% and a 0.005% (w/v) extract of the invention, as obtained in Example 1, or of 500 µM vitamin C (reference antioxidant), before incorporation of the H2DCF-DA probe (incubation for 1 hour).

The keratinocytes were then stimulated with UV at 2400 J/m$^2$ (2000 J/m$^2$ UVB and 400 J/m$^2$ UVA) then returned to culture in the presence of a 0.001% and a 0.005% (w/v) extract of the invention, as obtained in Example 1, or of 500 µM vitamin C, for 15 minutes at 37° C.

The production of reactive oxygen species (ROS) was evaluated by measurement of fluorescence and the value obtained was normalized to the quantity of cells obtained using an MTT cell viability assay.

The results were statistically analysed by one-way ANOVA followed by Tukey's test (GraphPad PRISM version 5.02 software, GraphPad Software, San Diego, Calif., USA).

Results and Conclusion

The extract of the invention significantly inhibited ROS production by keratinocytes in response to UV-induced (2400 J/m$^2$) oxidant stress (Table 17).

TABLE 17

ROS production in keratinocytes treated by UV at 2400 J/m$^2$

| | ROS (fluorescence intensity/MTT) | % change | Significance |
|---|---|---|---|
| Control cells | 30936 ± 4925 | | |
| Irradiated cells (UV 2400 J/m$^2$) | 43038 ± 5735 | 39 | $$$ |
| Reference (vitamin C) | 26005 ± 3723 | −40 | *** |
| Extract of the invention (0.001%) | 22564 ± 3849 | −48 | *** |
| Extract of the invention (0.005%) | 19614 ± 4576 | −54 | *** |

$$$ $p < 0.001$ vs control without UVs
*** $p < 0.001$ vs control with UVs
One-way ANOVA followed by Tukey's test 5. Protection Against the Effects of Chemical Stress Effect on PMA-Induced Production of PGE2:

The anti-inflammatory protection of an extract of the invention with respect to a chemical molecule, PMA, was studied by analysis of the release of prostaglandin 2 (PGE2).

Materials and Methods:

Normal human keratinocytes were pretreated with a 0.002% and a 0.005% extract of the invention, as obtained in Example 1, and with 10$^{-6}$ M indomethacin (anti-inflammatory control of the prostaglandin pathway) for 24 hours at 37° C., in order to be able to measure a level of protection of the active agent with respect to inflammation by 0.1 µg/ml PMA (phorbol 12-myristate 13-acetate) used on these same cell monolayers for a further 24 hours. At the end of the treatment, the supernatants are collected and an assay of prostaglandin E2 (PGE2; R&D Systems) is performed. Staining, proportional to the amount of PGE2, was measured by reading the optical density (OD) at 450 nm.

The significance of the results was verified by Student's t-test.

Results:

The results are presented in Table 18. These results show that the extract of the invention at both concentrations significantly decreased PGE2 release with respect to induction by 0.1 µg/ml PMA.

The extract of the invention thus has antioxidant, antiradical, antipollution and antiaging activity.

TABLE 18

PGE2 production in PMA-treated keratinocytes

| | PGE2 (pg/ml) | Inhibition | |
|---|---|---|---|
| Control cells | 39 ± 0 | 100% | *** |
| PMA (0.1 µg/ml) | 113806 ± 11441 | 0% | |
| Indomethacin (10$^{-6}$M) | 52 ± 8 | 100% | *** |
| Extract of the invention (0.002%) | 35750 ± 2192 | 69% | ** |
| Extract of the invention (0.005%) | 30382 ± 2401 | 73% | ** |

** $0.001 < p < 0.01$ and
*** $p < 0.001$ vs PMA-stimulated cells Student's t-test 6. Protection Against the Effects of Ageing The repeated action of environmental stresses such as pollution, the harmful effects of the sun, chemical molecules and all other forms of induction of oxidant stress, lead to degradation of the dermal matrix and thus to premature skin ageing.

An extract of the invention was analysed on a model of cell ageing in order to analyse their actions with respect to proteins which are underexpressed or overexpressed with age.

Materials and Methods:

Keratinocytes are cultured, and trypsinized each week, for 4 weeks in culture medium inducing an ageing phenotype ("pro-age" medium) optionally in the presence of a 0.000025% DM extract of the invention, as obtained in Example 1.

At the end of 3 weeks of culture/passages, a proteomic analysis is performed. The analysis grouped the proteins of the various cellular pathways into six domains: metabolism, apoptosis, detoxification, protein catabolism and protein synthesis.

Results and Conclusion

The results are presented in Table 19. In this context of induction of ageing, the extract of the invention stimulated and/or protected the expression of several proteins involved mainly in cellular detoxification/protection and immune defences:

Cellular Detoxification and Protection:
Stimulation of peroxiredoxin 2 (PRDX2): an antioxidant enzyme playing a role in cellular protection against damage caused by intracellular ROS.
Stimulation of carbonyl reductase 1 (CBR1): a dehydrogenase/reductase which reduces carbonyl compounds (medicinal products) and intervenes in detoxification during lipid peroxidation. The latter is inhibited under the "pro-age" conditions and is stimulated by the extract of the invention under these conditions.
Inhibition of aldehyde dehydrogenase 2 (ALDH2): a mitochondrial enzyme playing a role in cell protection and differentiation which catalyses/detoxifies aldehyde/carbonyl molecules (medicinal products, pollution, etc.). This protein is stimulated under the "pro-age" conditions, and the extract of the invention restores its expression to a basal level.
Stimulation of fatty acid-binding protein 5 (FABP5): a chaperone protein mainly expressed in the epidermis and involved in regulation of lipid homeostasis and thus playing a role in the barrier function. The "pro-age" conditions inhibit its expression, which is restored by passion fruit polyphenols.

Stimulation of proteasome β2 and β6 subunits (PSMB2 and PSMB6): Proteasomes are involved in the removal of damaged/oxidized proteins and in the replacement of intracellular proteins. The proteasome consists of α and β subunits which, amongst other things, cleave damaged proteins on the level of glutamine (β6) and on the level of trypsin (β2). Age decreases proteasome activity, which leads to an accumulation of damaged/oxidized proteins; this age effect is found under the "pro-age" conditions, and under these conditions the extract of the invention stimulates expression of these two proteasome subunits.

Immune Defence:

Inhibition of beta-2-microglobulin (B2MG): a small surface protein (epidermis) involved in the immune response. It is part of the major histocompatibility complex and is overexpressed in disease conditions, thus producing interleukins, notably 6 and 8, as well as 10, which is an immunosuppressive interleukin. Here, under conditions inducing ageing, its expression is increased. The extract of the invention prevents this increase.

Inhibition of lectin, mannose-binding, 1 (LMAN1): a protein participating in the immune response by enabling phagocytosis of apoptotic cells and of pathogens. A deficiency in this gene entails an increase in cell debris in the skin. It is scarce, if present at all, in the basal state and is increased in inflammatory conditions (e.g., UV). Under the "pro-age" conditions, its expression is increased and modulated under the action of the extract of the invention.

TABLE 19

Protein expression (in %) of markers involved in detoxification and in immunity

| Proteins | % induction with respect to normal medium | | % induction with respect to "pro-age" medium | |
|---|---|---|---|---|
| | "Pro-age" medium | Extract of the invention (0.000025%) | "Pro-age" medium | Extract of the invention (0.000025%) |
| Peroxiredoxin 2 (PRDX2) | 11.46 | 16.68 | 0.00 | 45.51 |
| Carbonyl reductase 1 (CBR1) | −15.87 | −7.46 | 0.00 | 52.99 |
| Aldehyde dehydrogenase 2 (ALDH2) | 46.81 | 4.97 | 0.00 | −89.38 |
| Fatty acid-binding protein 5 (FABP5) | −24.82 | 4.68 | 0.00 | 118.87 |
| Proteasome β2 (PSMB2) | −21.15 | −10.96 | 0.00 | 48.21 |
| Proteasome β6 (PSMB6) | −16.85 | −10.92 | 0.00 | 35.21 |
| Beta-2-microglobulin (B2MG) | 31.16 | −0.57 | 0.00 | −101.83 |
| Lectin, mannose-binding, 1 (LMAN1) | 40.13 | 3.71 | 0.00 | −90.75 |

7. Conclusion

These various tests show an anti-inflammatory, antioxidant, antipollution and thus antiaging effect of the polyphenolic extract of the invention.

Example 4: Evaluation of In Vivo Efficacy of the Passion Flower Polyphenol Active Agent Versus Placebo by Measurement of the Amount of MDA, SOD, Catalase (CAT) and Carbonylated Proteins Study Design:
Double-blind study.
Comparative, randomized study
Population:
Two groups of 30 Asian female subjects (1 active agent group and 1 placebo group), between 30 and 50 years of age, of all skin types, living in a polluted environment.
Use:
The products are applied to one side of the face, by the subjects themselves, at home, twice per day (morning and evening) for 28 days.
Study Protocol:

TABLE 20

Protocol of the clinical study

| Evaluation | T0 | T 28 days |
|---|---|---|
| Hair sampling | X | X |
| Biological sampling of the cheeks for MDA, CAT, SOD | X | X |
| Biological sampling of the cheeks for carbonylated proteins | X | X |

Mean Real Age Per Panel:
Panel total: 39.9 years (between 30 and 50 years)
Composition Administered:

| Material name | INCI EU | % material |
|---|---|---|
| PURIFIED WATER R&D | AQUA | 75.12 |
| SODIUM EDETATE | DISODIUM EDTA | 0.10 |
| BUTYLENE GLYCOL | BUTYLENE GLYCOL | 3.00 |
| CARBOPOL ULTREZ 10 | CARBOMER | 0.60 |
| OCTANEDIOL XI | CAPRYLYL GLYCOL | 0.30 |
| EMULIUM DELTA | CETYL ALCOHOL GLYCERYL STEARATE PEG-75 STEARATE CETETH-20 STEARETH-20 | 3.50 |
| ISONONYL ISONONANOATE | ISONONYL ISONONANOATE | 10.00 |
| PURE CETYL ALCOHOL | CETYL ALCOHOL | 0.50 |
| CAPRYLOYL GLYCINE | CAPRYLOYL GLYCINE | 0.80 |
| SODIUM HYDROXIDE XI | AQUA SODIUM HYDROXIDE | 1.08 |
| PURIFIED WATER R&D | AQUA | 2.00 |
| PURIFIED WATER R&D | AQUA | 3.00 |
| | | 100.00 |

| Material name | INCI EU | % material |
|---|---|---|
| PLACEBO | | 97 |
| PASSION FRUIT POLYPHENOLS 1 KG | AQUA PROPANEDIOL PASSIFLORA EDULIS FRUIT EXTRACT | 3 |
| | | 100 |

1. Evaluation of the Pollution Received by the Subject at T0 and T28

At T0 and T28, a 1-cm lock of hair was taken from the scalp. A biochemical analysis was performed in order to determine the heavy-metal exposure of the subjects at each time point. The analysis involved 10 subjects, 5 from each panel.

Figure 9:
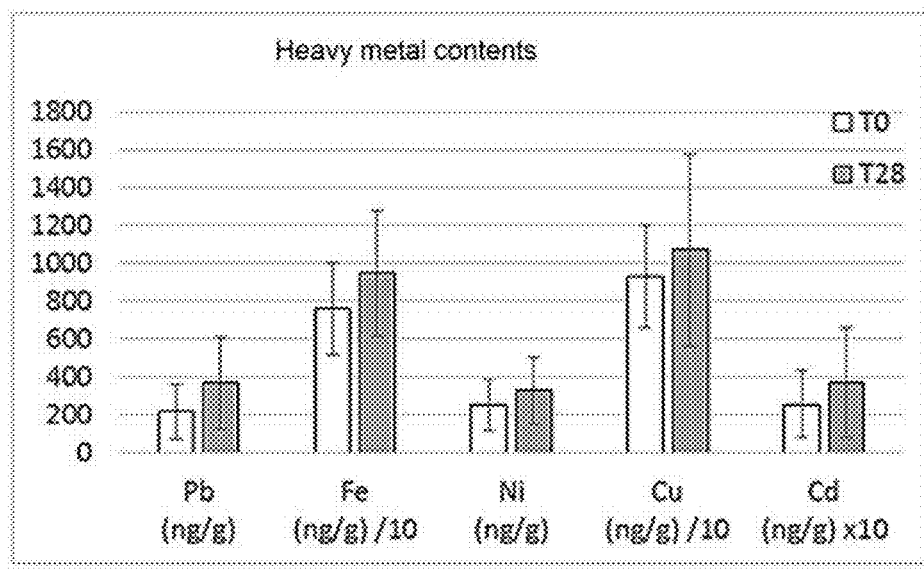
FIG. 9 shows the change in heavy metal contents at T0 and at T28 in the studied subjects.

The results (Table 21 and FIG. 9) show a constant amount of heavy metals or a slight increase. It can be concluded that the subjects' exposure to pollution did not decrease during the study, ruling out the hypothesis of a beneficial effect due only to a variation in pollution.

TABLE 21

Heavy metal contents

| | Pb (ng/g) | Fe (ng/g) | Ni (ng/g) | Cu (ng/g) | Cd (ng/g) |
|---|---|---|---|---|---|
| T0 | 218.5 | 7603.9 | 249.7 | 9283.8 | 25.5 |
| T28 | 366 | 9487 | 328 | 10711 | 37 |
| Significant difference | Yes $p = 0.0098$ | Yes $p = 0.0488$ | No $p = 0.0840$ | No $p = 0.2324$ | Yes $p = 0.0019$ |

2. Evaluation of the Amount of MDA, CAT and SOD at T0 and T28

At T0 and T28, a swab was taken from each cheek of the subjects. A biochemical analysis was performed in order to determine the amount of MDA, CAT and SOD. The analysis involved 30 subjects, 15 from each panel.

Figure 10A:
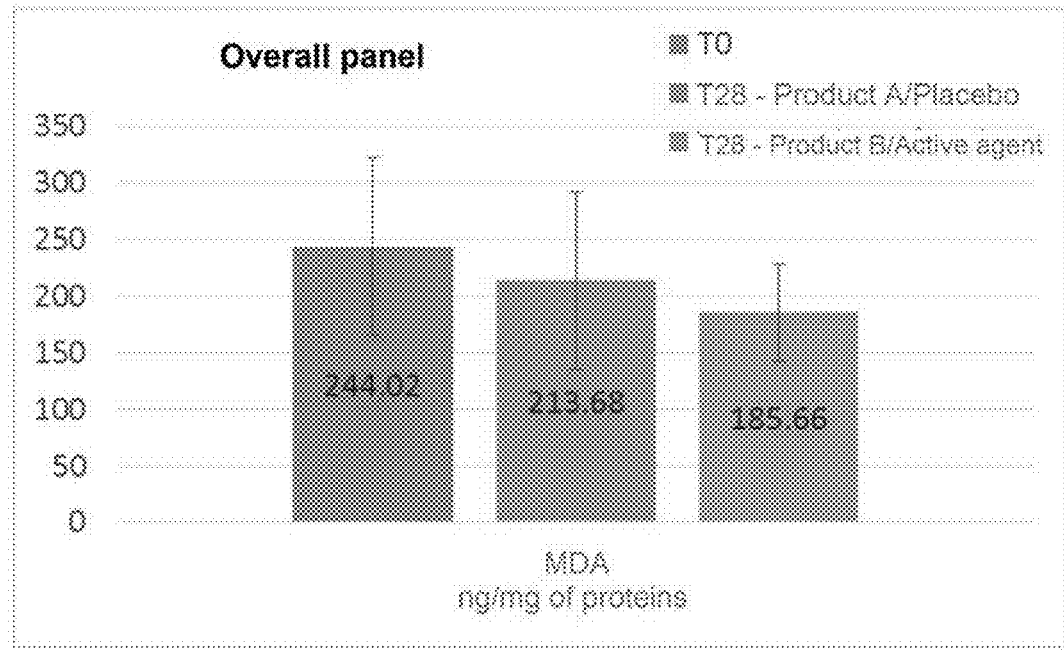
FIG. 10 shows the change in MDA (FIG. 10A), catalase and SOD (FIG. 10B) contents, expressed as U/mg of proteins, at T0 and at T28 in subjects having received the placebo or having received the active agent.
Figure 10B:
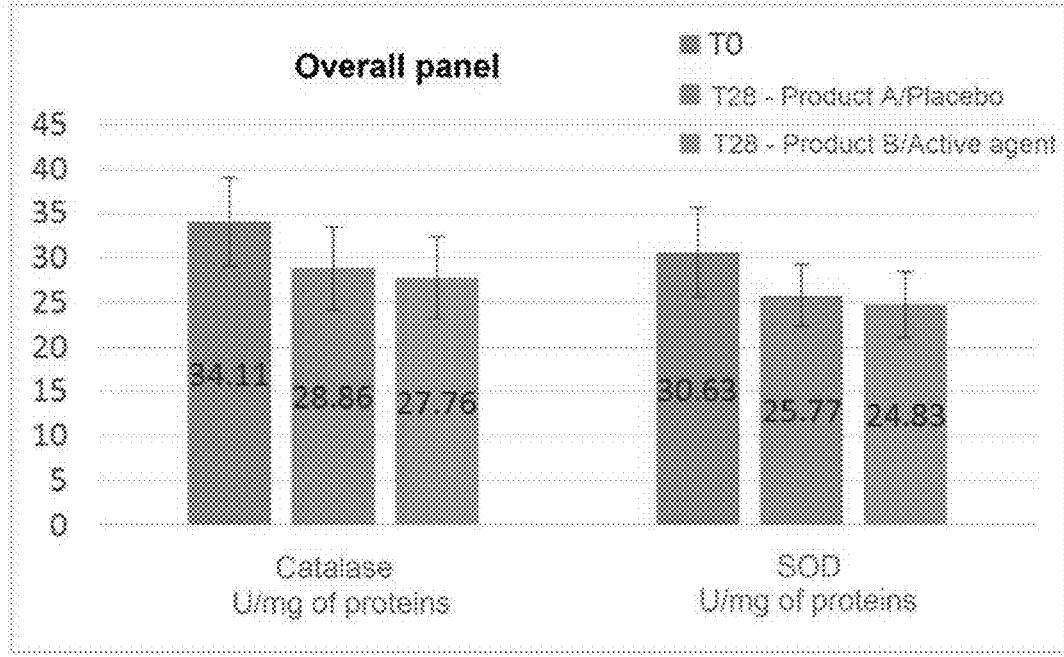

The amount of MDA, CAT and SOD significantly decreases between T0 and T28 for the active agent and the placebo, with a significantly larger decrease for the active agent (Table 22 and FIGS. 10A and 10B).

TABLE 22

MDA, CAT and SOD contents at T0 and T28

| | MDA | | CAT | | SOD | |
|---|---|---|---|---|---|---|
| | Placebo | Active agent | Placebo | Active agent | Placebo | Active agent |
| T0 | 244.0 ± 77.9 | 244.0 ± 77.9 | 34.1 ± 4.98 | 34.1 ± 4.98 | 30.6 ± 5.0 | 30.6 ± 5.0 |
| T28 | 213.7 ± 65.1 | 185.7 ± 56.3 | 28.9 ± 4.7 | 27.8 ± 4.6 | 25.8 ± 3.4 | 24.8 ± 3.7 |
| % change | −12.4% | −23.9% | −15.4% | −18.6% | −15.9% | −18.9% |
| Significance T28-T0 | Yes $p < 0.01$ | Yes $p < 0.01$ | Yes $p < 0.01$ | Yes $p < 0.01$ | Yes $p < 0.01$ | Yes $p < 0.01$ |
| Significance Placebo vs Active agent | Yes $p < 0.01$ | | Yes $p < 0.01$ | | Yes $p < 0.01$ | |

3. Evaluation of the Amount of Carbonylated Proteins at T0 and T28

At T0 and T28, D-Squame sampling was performed on each cheek of the subjects. Biochemical staining was performed in order to determine the amount of carbonylated proteins. The analysis involved 20 subjects, 10 from each panel.

Figure 11A:
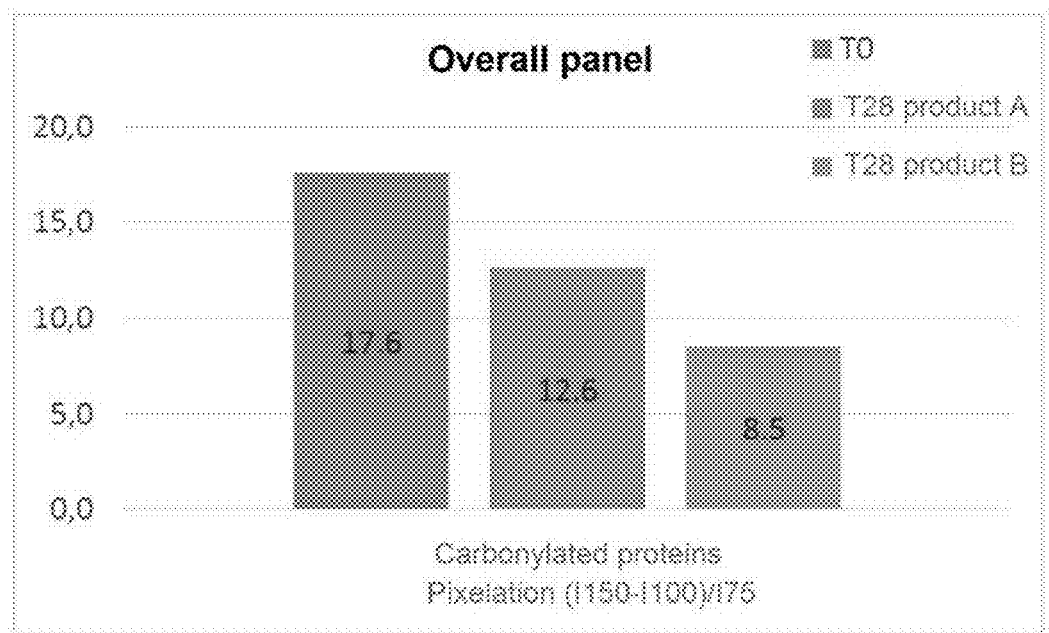
FIG. 11A is a bar chart and FIG. 11B shows photographs of cell layers with fluorescent staining of carbonylated proteins. Quantification is then performed by image analysis.
Figure 11B:
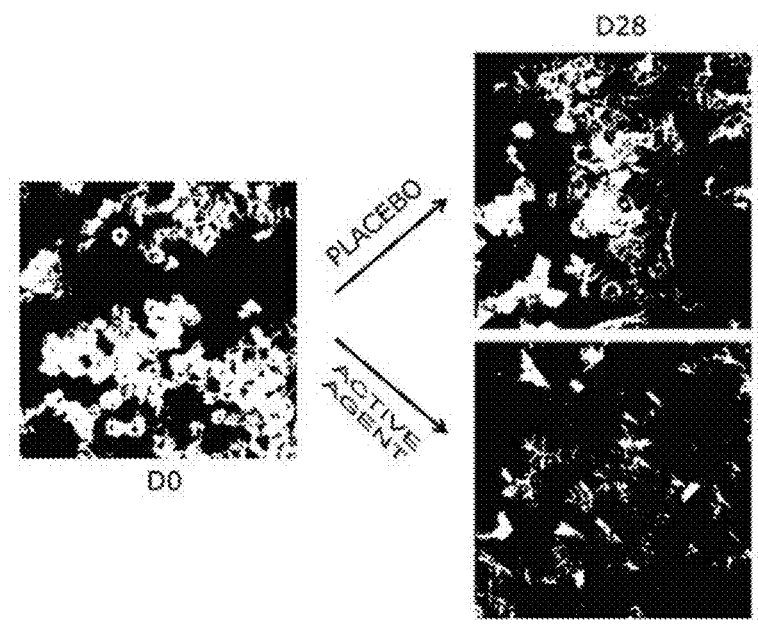

The amount of carbonylated proteins significantly decreases between T0 and T28 for the active agent and the placebo, with a significantly larger decrease for the active agent (Table 23 and FIGS. 11A and 11B).

TABLE 23

Carbonylated protein contents at T0 and T28

| | Carbonylated proteins | |
|---|---|---|
| | Placebo | Active agent |
| T0 | 17.6 ± 5.6 | 17.6 ± 5.6 |
| T28 | 12.6 ± 7.9 | 8.5 ± 5.5 |
| % change | −28.1% | −51.5% |
| Significance T28-T0 | Yes $p < 0.01$ | Yes $p < 0.01$ |
| Significance Placebo vs Active agent | Yes $p = 0.01$ | |

4. Summary of Biochemical Measurements

The results show an antiradical/detoxifying efficacy both on the overall panel and on the non-smoker and smoker subpanels.

The active agent substitutes for the skin's natural defences, SOD and CAT, thus leading to a smaller amount of residues resulting from the detoxification process (MDA).

The results for carbonylated proteins confirm this antiradical/detoxifying action.

5. Summary of Efficacy

The active agent (3%) showed a significant efficacy on the following parameters:

Amount of MDA in the cheek

The active agent induced the following effects on the amount of MDA measured from the biological sample of the cheek:

For the overall panel (30 subjects), a significant decrease of 23.9%. The effect observed is significant relative to the effect observed with the placebo.

Amount of SOD in the cheek

The active agent induced the following effects on the amount of SOD measured from the biological sample of the cheek:

For the overall panel (30 subjects), a significant decrease of 18.6%. The effect observed is significant relative to the effect observed with the placebo.

Amount of CAT in the cheek

The active agent induced the following effects on the amount of CAT measured from the biological sample of the cheek:

For the overall panel (30 subjects), a significant decrease of 18.9%. The effect observed is significant relative to the effect observed with the placebo.

Amount of carbonylated proteins in the cheek

The active agent induced the following effects on the amount of carbonylated proteins measured from the biological sample of the cheek:

For the overall panel (20 subjects), a significant decrease of 51.5%. The effect observed is significant relative to the effect observed with the placebo.

All of these results show significant effects in terms of detoxification.

Example 5: Compositions for Application Via the Topical Route

Several compositions for application via the topical route are presented below. The polyphenolic extract of passion flower seeds, of Example 1 or 2, can be incorporated in various cosmetic products, such as cleansing waters, oil-in-water emulsions, water-in-oil emulsions, oils, milks, lotions, shampoos, foaming products and sprays, the compositions of which are presented below by way of example.

| SENSITIVE SKIN CLEANSING WATER | |
|---|---|
| Raw material/Brand name or INCI name | % |
| CAPRYLOYL GLYCINE | From 0 to 1% |
| SODIUM HYDROXIDE | From 0 to 1% |
| SEQUESTRANT | From 0 to 1% |
| BUTYLENE GLYCOL | From 1 to 5% |
| BETA CAROTENE | From 0 to 2% |
| POLYPHENOLIC EXTRACT OF PASSION FLOWER | From 0.001 to 10% |
| PRESERVATIVES | From 0 to 1% |
| PEG-32 | From 1 to 5% |
| PEG-7 PALM COCOATE | From 1 to 5% |
| ZINC GLUCONATE | From 0 to 1% |
| CITRIC ACID | From 0 to 1% |
| PURIFIED WATER | QS 100% |
| FRAGRANCE | From 0 to 1% |
| POLOXAMER 184 | From 1 to 5% |

| Raw material/Brand name or INCI name | % |
|---|---|
| LIQUID ISOPARAFFIN | From 5 to 20% |
| ISOCETYL STEARATE | From 5 to 20% |
| AL - MG HYDROXY STEARATE | From 5 to 20% |
| ABIL WE 09 | From 1 to 5% |
| GLYCEROL | From 1 to 5% |
| VASELINE OIL | From 1 to 5% |
| MICRONIZED ZINC OXIDE | From 1 to 5% |
| BUTYLENE GLYCOL | From 1 to 5% |
| RETINOL | From 0 to 1% |
| VITAMIN C | From 0 to 5% |
| POLYPHENOLIC EXTRACT OF PASSION FLOWER | From 0.01 to 10% |
| ISONONYL ISONONANOATE | From 1 to 5% |
| BEESWAX | From 1 to 5% |
| SODIUM TARTRATE | From 1 to 5% |
| SODIUM CHLORIDE | From 0 to 5% |
| GLYCINE | From 1 to 5% |
| PRESERVATIVES | From 0 to 1% |
| CHOLESTEROL | From 0 to 1% |
| PHYTOSPHINGOSINE | From 0 to 1% |
| TARTARIC ACID | From 0 to 1% |
| PURIFIED WATER | QS 100% |

The invention claimed is:

1. A method for preventing and/or treating:
disorders or pathologies of the skin and/or of the mucous membranes and/or of the skin appendages, advantageously inflammatory reactions, oxidation reactions, disorders relating to radical attacks optionally linked to pollution, disorders of the barrier or of homeostasis, of ageing, notably of chronological and/or actinic ageing, of the skin and/or of the mucous membranes and/or of the skin appendages, and/or
vascular disorders, and/or
damaged adipose tissue,
said method comprising administering to a subject in need thereof of a composition comprising an effective amount of a polyphenolic extract of seeds of passion flower, in particular of *Passiflora incarnata* or *Passiflora edulis*, and a suitable excipient, said polyphenolic extract of seeds of passion flower comprising at least 30 wt % polyphenols, expressed as gallic acid equivalents, relative to the weight of the dry extract, and at least 10 wt % organic acids, relative to the weight of the dry extract.

2. The method of claim 1, wherein said polyphenolic extract of passion flowers seeds comprises at least 35 wt % polyphenols, expressed as gallic equivalents, relative to the weight of the dry extract.

3. The method of claim 1, wherein said polyphenolic extract of passion flowers seeds comprises at least 40 wt % polyphenols, expressed as gallic equivalents, relative to the weight of the dry extract.

4. The method of claim 1, wherein at least 50 wt % of said polyphenols are catechin derivatives, expressed as gallic acid equivalents, relative to the weight of polyphenols in the dry extract.

5. The method of claim 1, wherein said organic acids are acetic acid, malic acid, citric acid or mixtures thereof.

6. The method of claim 1, wherein said polyphenolic extract of passion flowers seeds is obtained by solid/liquid extraction of passion flowers seeds in a solvent selected from the binary mixtures water/glycerol, water/glycol, and mixtures thereof.

7. The method of claim 1, wherein said polyphenolic extract of passion flowers seeds is obtained by solid/liquid extraction of passion flowers seeds in a solvent selected from the binary mixtures water/glycerol, water/glycol, and mixtures thereof, in a proportion of 30% to 90% of glycerol and/or of glycol in water.

8. The method of claim 1, wherein said polyphenolic extract of passion flowers seeds is obtained by solid/liquid extraction of passion flowers seeds in a solvent selected from the binary mixtures water/glycerol, water/glycol, and mixtures thereof, in a proportion of 50% to 90% of glycerol and/or of glycol in water.

9. The method of claim 1, wherein said polyphenolic extract of passion flowers seeds is obtained by solid/liquid extraction of passion flowers seeds in a solvent selected from the binary mixtures water/glycerol, water/glycol, and mixtures thereof, in a proportion of 60% to 80% of glycerol and/or of glycol in water.

10. The method of claim 1, wherein said composition comprises from 0.001 to 10 wt % of said polyphenolic extract of passion flowers seeds, the weight of the extract being expressed as dry extract, relative to the total weight of the composition.

11. The method of claim 1, wherein said composition comprises from 0.01 to 5 wt % of said polyphenolic extract of passion flowers seeds, the weight of the extract being expressed as dry extract, relative to the total weight of the composition.

12. A method for cosmetic care of the skin and/or of the skin appendages and/or of the mucous membranes, for improving the condition and/or the appearance thereof, comprising administering to a subject in need thereof a composition comprising an effective amount of a polyphenolic extract of seeds of passion flower, in particular of *Passiflora incarnata* or *Passiflora edulis*, and a suitable excipient, said polyphenolic extract of seeds of passion flower comprising at least 30 wt % polyphenols, expressed as gallic acid equivalents, relative to the weight of the dry extract, and at least 10 wt % organic acids, relative to the weight of the dry extract.

13. The method of claim 12, wherein said polyphenolic extract of passion flowers seeds comprises at least 35 wt % polyphenols, expressed as gallic equivalents, relative to the weight of the dry extract.

14. The method of claim 12, wherein said polyphenolic extract of passion flowers seeds comprises at least 40 wt % polyphenols, expressed as gallic equivalents, relative to the weight of the dry extract.

15. The method of claim 12, wherein at least 50 wt % of said polyphenols are catechin derivatives, expressed as gallic acid equivalents, relative to the weight of polyphenols in the dry extract.

16. The method of claim 12, wherein said organic acids are acetic acid, malic acid, citric acid or mixtures thereof.

17. The method of claim 12, wherein said polyphenolic extract of passion flowers seeds is obtained by solid/liquid extraction of passion flowers seeds in a solvent selected from the binary mixtures water/glycerol, water/glycol, and mixtures thereof.

18. The method of claim 12, wherein said polyphenolic extract of passion flowers seeds is obtained by solid/liquid extraction of passion flowers seeds in a solvent selected from the binary mixtures water/glycerol, water/glycol, and mixtures thereof, in a proportion of 30% to 90% of glycerol and/or of glycol in water.

19. The method of claim 12, wherein said polyphenolic extract of passion flowers seeds is obtained by solid/liquid extraction of passion flowers seeds in a solvent selected from the binary mixtures water/glycerol, water/glycol, and mixtures thereof, in a proportion of 50% to 90% of glycerol and/or of glycol in water.

20. The method of claim 12, wherein said polyphenolic extract of passion flowers seeds is obtained by solid/liquid extraction of passion flowers seeds in a solvent selected from the binary mixtures water/glycerol, water/glycol, and mixtures thereof, in a proportion of 60% to 80% of glycerol and/or of glycol in water.

21. The method of claim 12, wherein said composition comprises from 0.001 to 10 wt % of said polyphenolic extract of passion flowers seeds, the weight of the extract being expressed as dry extract, relative to the total weight of the composition.

22. The method of claim 12, wherein said composition comprises from 0.01 to 5 wt % of said polyphenolic extract of passion flowers seeds, the weight of the extract being expressed as dry extract, relative to the total weight of the composition.

* * * * *